US012440640B2

(12) United States Patent
Rummery

(10) Patent No.: US 12,440,640 B2
(45) Date of Patent: Oct. 14, 2025

(54) MODULAR HEADGEAR

(71) Applicant: RESMED PTY LTD, Bella Vista (AU)

(72) Inventor: Gerard Michael Rummery, Woodford (AU)

(73) Assignee: ResMed Pty Ltd, Bella Vista (AU)

( * ) Notice: Subject to any disclaimer, the term of this patent is extended or adjusted under 35 U.S.C. 154(b) by 864 days.

(21) Appl. No.: 17/631,354

(22) PCT Filed: Jul. 31, 2020

(86) PCT No.: PCT/AU2020/050787
§ 371 (c)(1),
(2) Date: Jan. 28, 2022

(87) PCT Pub. No.: WO2021/016673
PCT Pub. Date: Feb. 4, 2021

(65) Prior Publication Data

US 2022/0323705 A1 Oct. 13, 2022

(30) Foreign Application Priority Data

Jul. 31, 2019 (AU) ................................ 2019902737

(51) Int. Cl.
*A61M 16/06* (2006.01)
*A61M 16/08* (2006.01)

(52) U.S. Cl.
CPC .... *A61M 16/0683* (2013.01); *A61M 16/0622* (2014.02); *A61M 16/0666* (2013.01); *A61M 16/0816* (2013.01); *A61M 16/0875* (2013.01)

(58) Field of Classification Search
CPC .......... A61M 16/0616; A61M 16/0622; A61M 16/0666; A61M 16/0683; A61M 16/0816; A61M 16/0875
See application file for complete search history.

(56) References Cited

U.S. PATENT DOCUMENTS

| | | | |
|---|---|---|---|
| 4,782,832 | A | 11/1988 | Trimble et al. |
| 4,944,310 | A | 7/1990 | Sullivan |

(Continued)

FOREIGN PATENT DOCUMENTS

| | | | |
|---|---|---|---|
| CN | 108434575 | A | 8/2018 |
| WO | WO 98/004310 | A1 | 2/1998 |

(Continued)

OTHER PUBLICATIONS

International Search Report for PCT/AU2020/050787 issued Nov. 2, 2020 (4 pages).

(Continued)

*Primary Examiner* — Joseph D. Boecker
(74) *Attorney, Agent, or Firm* — Nixon & Vanderhye P.C.

(57) ABSTRACT

A patient interface to deliver air at a positive pressure to a patients airways, including nasal and mouth cushions; a positioning and stabilizing structure to provide a force to hold the nasal seal-forming structure or the nasal seal and the mouth seal-forming structure in position on a patients head, the positioning and stabilizing structure comprising nasal and oro-nasal headgear configurations and including left and right headgear sections, a pair of nasal headgear clips connecting the nasal headgear to the left and right headgear sections at a first angle and/or position applying nasal headgear forces to the nasal seal-forming structure, and a pair of oro-nasal headgear clips connecting the oro-nasal headgear to the left and right headgear sections at a second angle and/or position applying oro-nasal forces to the mouth seal forming structure in the oro-nasal configuration. The first angle and/or position is different than the second angle and/or position.

43 Claims, 33 Drawing Sheets

(56) References Cited

U.S. PATENT DOCUMENTS

| | | | | |
|---|---|---|---|---|
| 6,532,959 | B1 | 3/2003 | Berthon-Jones | |
| 6,581,594 | B1 | 6/2003 | Drew et al. | |
| 7,866,944 | B2 | 1/2011 | Kenyon et al. | |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 2006/0237017 | A1 * | 10/2006 | Davidson .......... | A61M 16/0683 128/205.25 |
| 2009/0044808 | A1 | 2/2009 | Guney et al. | |
| 2009/0050156 | A1 | 2/2009 | Ng et al. | |
| 2009/0114229 | A1 * | 5/2009 | Frater ............... | A61M 16/0683 128/205.25 |
| 2009/0133696 | A1 * | 5/2009 | Remmers .......... | A61M 16/0493 128/204.26 |
| 2009/0241961 | A1 * | 10/2009 | McAuley ............ | A61M 16/024 128/207.18 |
| 2010/0000534 | A1 | 1/2010 | Kooij et al. | |
| 2013/0133646 | A1 | 5/2013 | Rose et al. | |
| 2013/0199537 | A1 * | 8/2013 | Formica ............ | A61M 16/0816 128/205.25 |
| 2016/0067441 | A1 * | 3/2016 | Bearne .............. | A61M 16/0605 128/205.25 |
| 2016/0271354 | A1 * | 9/2016 | Grashow ........... | A61M 16/0683 |
| 2017/0274167 | A1 | 9/2017 | Huddart et al. | |
| 2018/0207385 | A1 | 7/2018 | Freestone et al. | |
| 2019/0022343 | A1 | 1/2019 | Kooij et al. | |
| 2022/0395660 | A1 * | 12/2022 | Scheiner ........... | A61M 16/0683 |

FOREIGN PATENT DOCUMENTS

| | | | | |
|---|---|---|---|---|
| WO | WO 98/034665 | A1 | 8/1998 | |
| WO | WO 2000/078381 | A1 | 12/2000 | |
| WO | WO 2004/073778 | A1 | 9/2004 | |
| WO | WO 2005/063328 | A1 | 7/2005 | |
| WO | WO 2006/074513 | A1 | 7/2006 | |
| WO | WO 2006/130903 | A1 | 12/2006 | |
| WO | WO 2009/052560 | A1 | 4/2009 | |
| WO | WO 2010/135785 | A1 | 12/2010 | |
| WO | WO 2012/171072 | A1 | 12/2012 | |
| WO | WO 2013/020167 | A1 | 2/2013 | |
| WO | WO-2017124155 | A1 * | 7/2017 | ............ A61M 16/06 |

OTHER PUBLICATIONS

Written Opinion of the ISA for PCT/AU2020/050787 issued Nov. 2, 2020 (6 pages).

"*Respiratory Physiology*", by John B. West, Lippincott Williams & Wilkins, $9^{th}$ edition published 2012 (8 pages).

First Office Action mailed Jun. 27, 2025 in Chinese Application No. 202080060778.5, with English translation, 22 pages.

* cited by examiner

Relatively Large
Positive Curvature

Relatively Small
Positive Curvature

Zero Curvature

Relatively Small
Negative Curvature

Relatively Large
Negative Curvature

MODULAR HEADGEAR

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATIONS

This application is the U.S. national phase of International Application No. PCT/AU2020/050787 filed Jul. 31, 2020 which designated the U.S. and claims priority to AU Provisional Application No. 2019902737 filed Jul. 31, 2019, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 $cmH_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 $cmH_2O$)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of the present technology relates to a patient interface including a cushion assembly including a seal-forming structure constructed and arranged to form a seal with the patient's nasal and/or oral airways, and a positioning and stabilizing structure to maintain the cushion in place on the patient's head during therapy.

An aspect of the present technology relates to a patient interface to deliver a flow of air at a positive pressure with respect to ambient air pressure to an entrance to a patient's airways including at least the entrance of a patient's nares while the patient is sleeping, to ameliorate sleep disordered breathing, the patient interface comprising:

- a nasal cushion forming at least part of a plenum chamber pressurizable to a therapeutic pressure, wherein the nasal cushion comprises a nasal seal-forming structure constructed and arranged to form a seal with a region of a patient's face surrounding the entrance to a patient's nares;
- a mouth cushion pressurizable to the therapeutic pressure, wherein the mouth cushion comprises a mouth seal-forming structure constructed and arranged to form a seal with a region of a patient's face surrounding the entrance to a patient's mouth;
- a positioning and stabilizing structure to provide a force to hold the nasal seal-forming structure or the nasal seal and the mouth seal-forming structure in a therapeutically effective position on a patient's head, the positioning and stabilizing structure comprising a nasal headgear configuration and an oro-nasal headgear configuration, the positioning and stabilizing structure including a left headgear section and a right headgear section each adapted to pass along a patient's cheek under a patient's eye and between the patient's eye and ear;
- a pair of nasal headgear clips to connect the nasal headgear to the left and right headgear sections at a first angle and/or position to ensure appropriate nasal headgear forces are applied to the nasal seal-forming structure when the nasal cushion alone is worn by the patient, and a pair of oro-nasal headgear clips to connect the oro-nasal headgear to the left and right headgear sections at a second angle and/or position to ensure appropriate oro-nasal forces are applied to the oro-nasal seal forming structure when the nasal cushion and the mouth cushion are worn by the patient, wherein the first angle and/or position is different than the second angle and/or position.

Another aspect of the present technology is to provide a modular headgear wherein a patient interface is convertible between a nasal mask and an oro-nasal mask, and different headgear configurations appropriate for each are provided. A nasal mask component may be the same for both the nasal mask and the oro-nasal mask, and the different headgear configurations may both connected to the nasal mask component (e.g., via headgear tubes), using first and second sets of clips that have predetermined orientations that position and/or angle one or more straps of the nasal headgear configuration in ways that are different than one or more straps of the oro-nasal headgear configuration. The set of clips for the oro-nasal headgear configuration may be permanently attached to the straps of the oro-nasal headgear configuration and the set of clips for the nasal headgear configuration may be permanently be attached to the straps of the nasal headgear configuration.

In examples, the patient interface can include one or more of the following features: (a) the oro-nasal headgear clips are permanently connected to the oro-nasal headgear and/or the nasal headgear clips are permanently connected to the nasal headgear; (b) the oro-nasal clips include indicia indicating use with the nasal/mouth cushion and/or oro-nasal headgear, and the nasal clips include indicia indicating use with the nasal cushion and/or nasal headgear; (c) the nasal headgear clips have shapes that are different than the shapes of the oro-nasal headgear clips; (d) each of the nasal headgear clips and the oro-nasal headgear clips is substantially wedge-shaped, with one main side following along the left/right headgear section, an opposite side for connection to the oro-nasal headgear, an upper side and a lower side, the upper side being wider than the lower side; (e) the main sides of the nasal and oro-nasal clips are identical, and the upper side of the nasal headgear clip is longer than the upper side of the oro-nasal headgear clip; (f) the oro-nasal headgear clips include slots that are configured to exclusively receive oro-nasal headgear straps of the oro-nasal headgear, and the nasal headgear clips are configured to exclusively receive nasal headgear straps of the nasal headgear; (g) the slots of the oro-nasal headgear clips have a different size/width compared to the slots of the nasal headgear clips; (h) the headgear clips include slots, and the slots in the nasal headgear clips are formed at lower portions of the nasal headgear clips, and the oro-nasal headgear clips are formed at upper portions of the oro-nasal headgear clips; (i) each of the left and right headgear sections includes a common connection element that is releasably connectable with the pair of nasal headgear clips and alternatively the pair of oro-nasal headgear clips; (j) the common connection element includes a groove or a slider; (k) the groove and/or the slider includes a stop to ensure proper depth and/or direction of connection; (l) the common connection element includes the groove, and each of the clips includes a slider; (m) each of the nasal headgear clips includes a nasal headgear clip slot that is substantially straight, and each of the oro-nasal headgear clips includes an oro-nasal headgear clip slot that is substantially straight, the nasal headgear clip slot being formed at a nasal clip slot angle relative to the common connection element, and the oro-nasal clip slot being formed at an oro-nasal clip slot angle that is different than the nasal clip slot angle relative to the common connection element; (n) each of the pair of nasal headgear clips and the pair of oro-nasal headgear clips includes a slot to receive a top strap of the nasal headgear or the oro-nasal headgear; (o) each of the pair of nasal headgear clips includes a nasal headgear slot, and each of the pair of oro-nasal headgear clips includes an oro-nasal headgear slot, each said nasal headgear slot being positioned at a slot angle and/or position relative to the left/right headgear section that is different than the slot angle and/or position of the oro-nasal headgear slots relative to the left/right headgear sections; (p) the oro-nasal headgear includes a pair of upper oro-nasal straps connectable to the oro-nasal headgear clips and the nasal headgear includes a pair of upper nasal straps connectable to the nasal headgear clips; (q) the oro-nasal headgear clips are configured to hold upper ends of the upper oro-nasal straps at an oro-nasal strap position, and the nasal headgear clips are configured to hold upper ends of the upper nasal straps at a nasal strap position, the oro-nasal strap position being different than the nasal strap position relative to the left/right headgear sections; (r) the oro-nasal strap position is higher than the nasal strap position; (s) the oro-nasal headgear clips are configured to hold upper ends of the upper oro-nasal straps at an oro-nasal strap angle, and the nasal headgear clips are configured to hold upper ends of the upper nasal straps at a nasal strap angle, the oro-nasal strap angle being different than the nasal strap angle relative to the left/right headgear sections; (t) the oro-nasal strap angle is smaller than the nasal strap angle; (u) the oro-nasal strap angle is less than the nasal strap angle relative to the patient's Frankfort horizontal; (v) the angle is measured from the lower part of the left/right headgear sections; (w) the mouth cushion includes a second nasal cushion, or the mouth cushion does not include the nasal cushion; (x) the mouth cushion and the nasal cushion are releasably connected to one another; (y) each of the left and right headgear sections includes a fabric strap; (z) each of the left and right headgear sections includes a hollow tube configured to convey pressurized gas at the therapeutic pressure from the rear or crown of the patient's head to the nasal cushion and/or the mouth cushion for breathing by the patient; (aa) each said hollow tube supports the nasal cushion and/or the mouth cushion in position on the patient's face; (ab) the patient interface is provided without a forehead support; (ac) the nasal headgear includes first and second straps that are connected to the nasal headgear clips; (ad) the first and second straps are permanently connected to the nasal headgear clips; (ae) the nasal headgear includes a center part having a split, forming upper and lower strap portions with a space in between and adapted to cup the occupit of the patient's head; (af) the oro-nasal headgear includes the nasal headgear and a bottom strap section that is releasably connected to the nasal headgear, the bottom strap section including ends that are connectable to the mouth cushion; (ag) the oro-nasal headgear includes a pair of upper straps each having an end connected to one of the oro-nasal headgear clips; (ah) the upper straps are permanently connected to the oro-nasal headgear clips; (ai) the oro-nasal headgear includes a bottom strap section adapted to pass under the patient's ears, the bottom strap section including a pair of ends attachable to the mouth cushion; (aj) the oro-nasal headgear includes a pair of upper straps connected to the bottom strap section at an angle that forms the general shape of a "V"; (ak) each of the ends of the bottom strap section is attached to a cushion clip or magnetic cushion clip that attaches to the mouth cushion; (al) the nasal headgear and the oro-nasal headgear are length adjustable; (am) each of the left and right headgear sections is releasably connected to the nasal cushion; (an) comprising a crown piece connecting the left and right headgear sections, the crown piece including an opening that receives a rotatable elbow; (ao) the nasal seal-forming structure comprises a nasal cradle cushion, a nasal cushion or pillows adapted to from a seal relative to the entrance of a patient's nose; and/or (ap) the mouth cushion includes an under the chin support, or does not include a chin support.

An aspect of the present technology relates to a CPAP system for providing gas at positive pressure for respiratory therapy to a patient, the CPAP system including an RPT device configured to supply a flow of gas at a therapeutic pressure, a patient interface, and an air delivery conduit configured to pass a flow of gas at therapeutic pressure from the RPT device to the patient interface.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 2A:
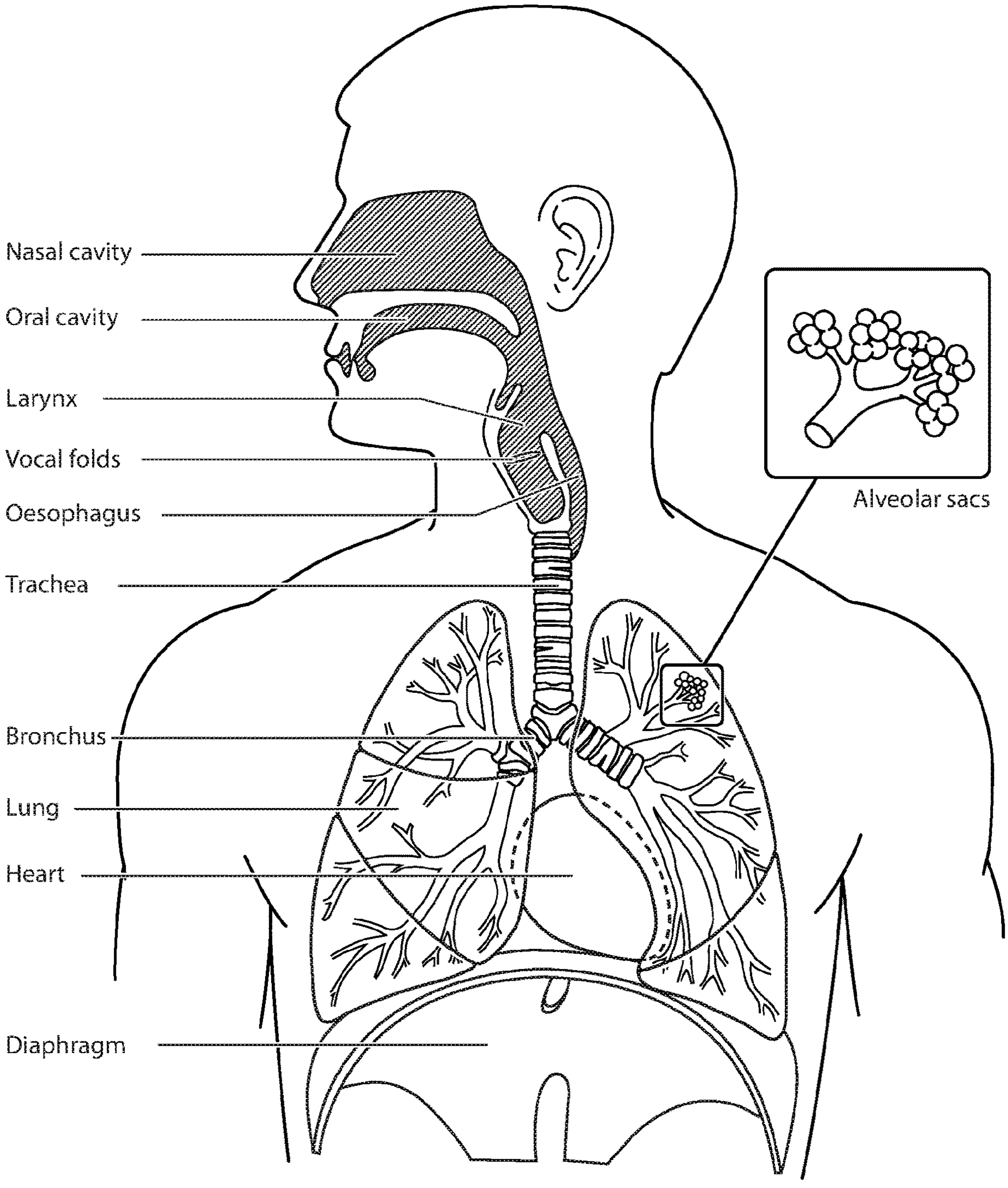
FIG. 2A shows an overview of a human respiratory system including the nasal and oral cavities, the larynx, vocal folds, oesophagus, trachea, bronchus, lung, alveolar sacs, heart and diaphragm.
Figure 2B:
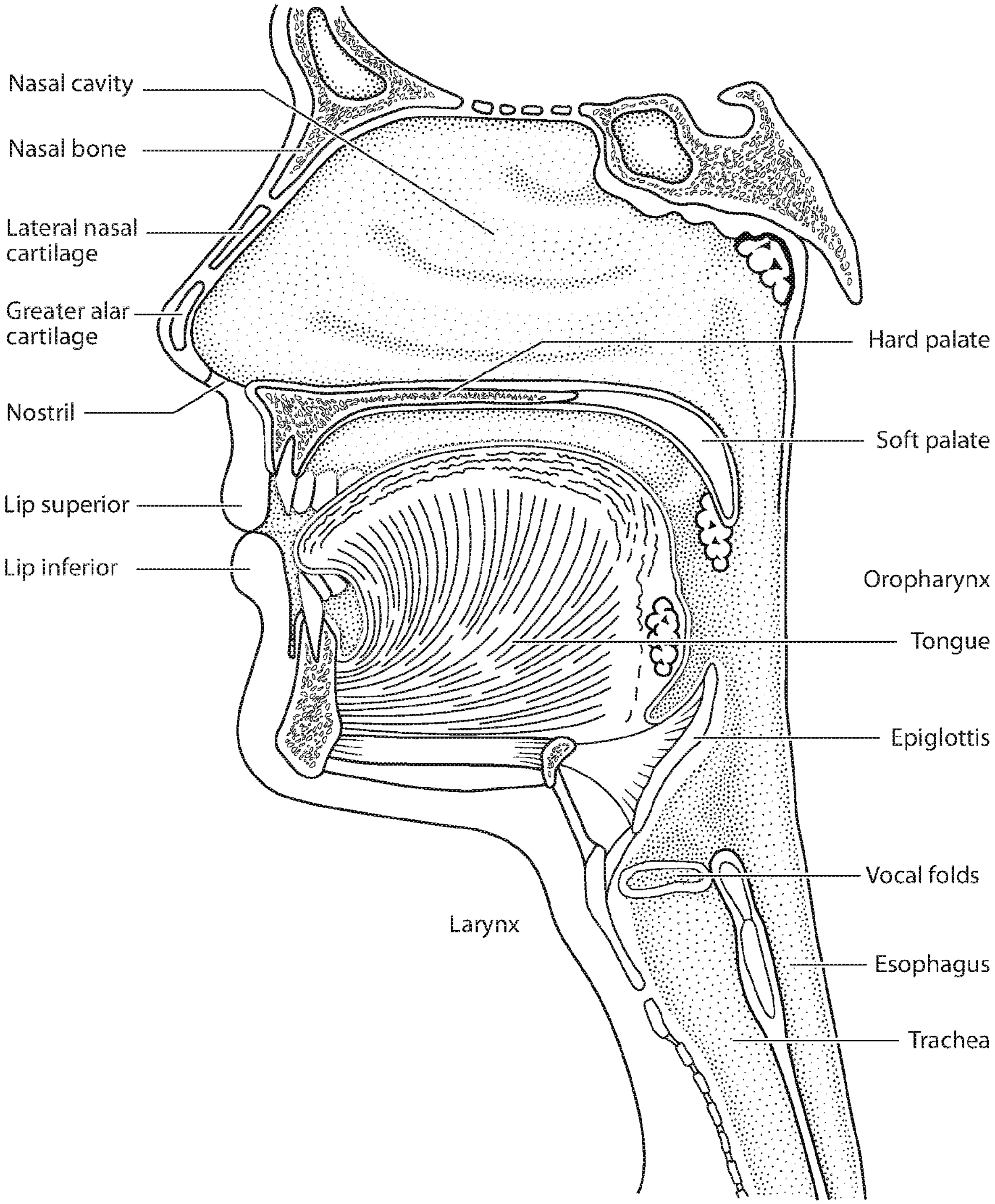
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
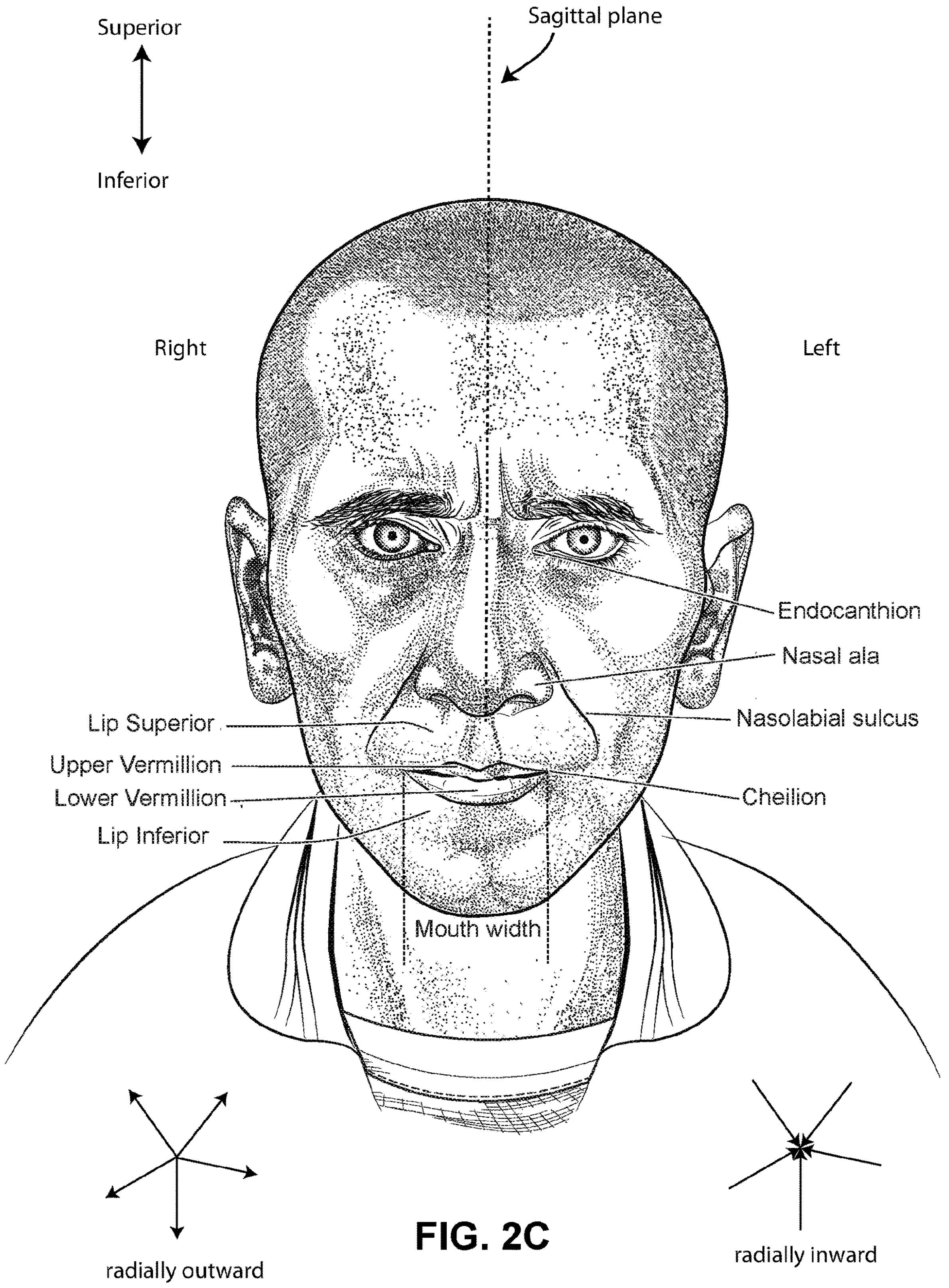
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
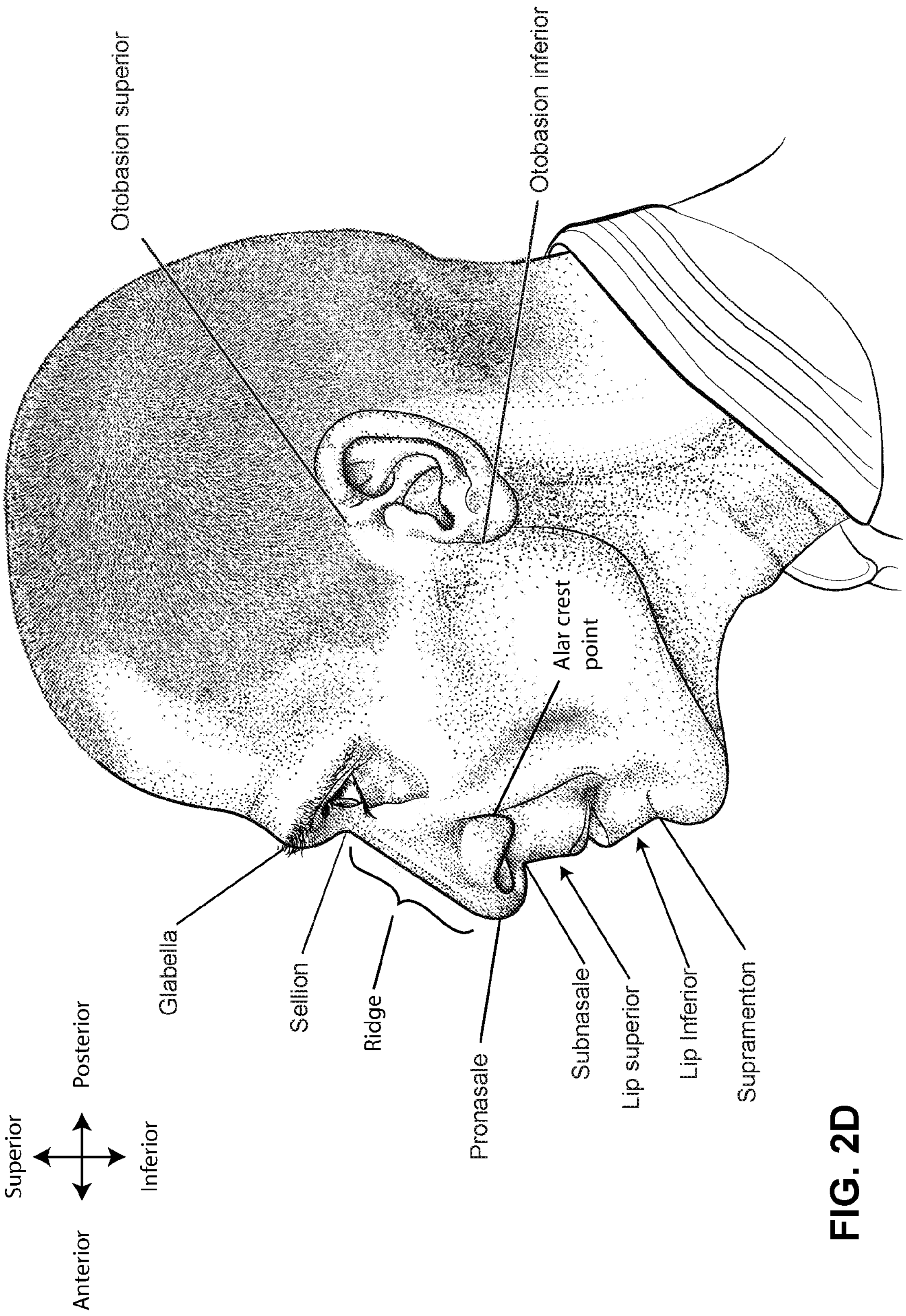
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
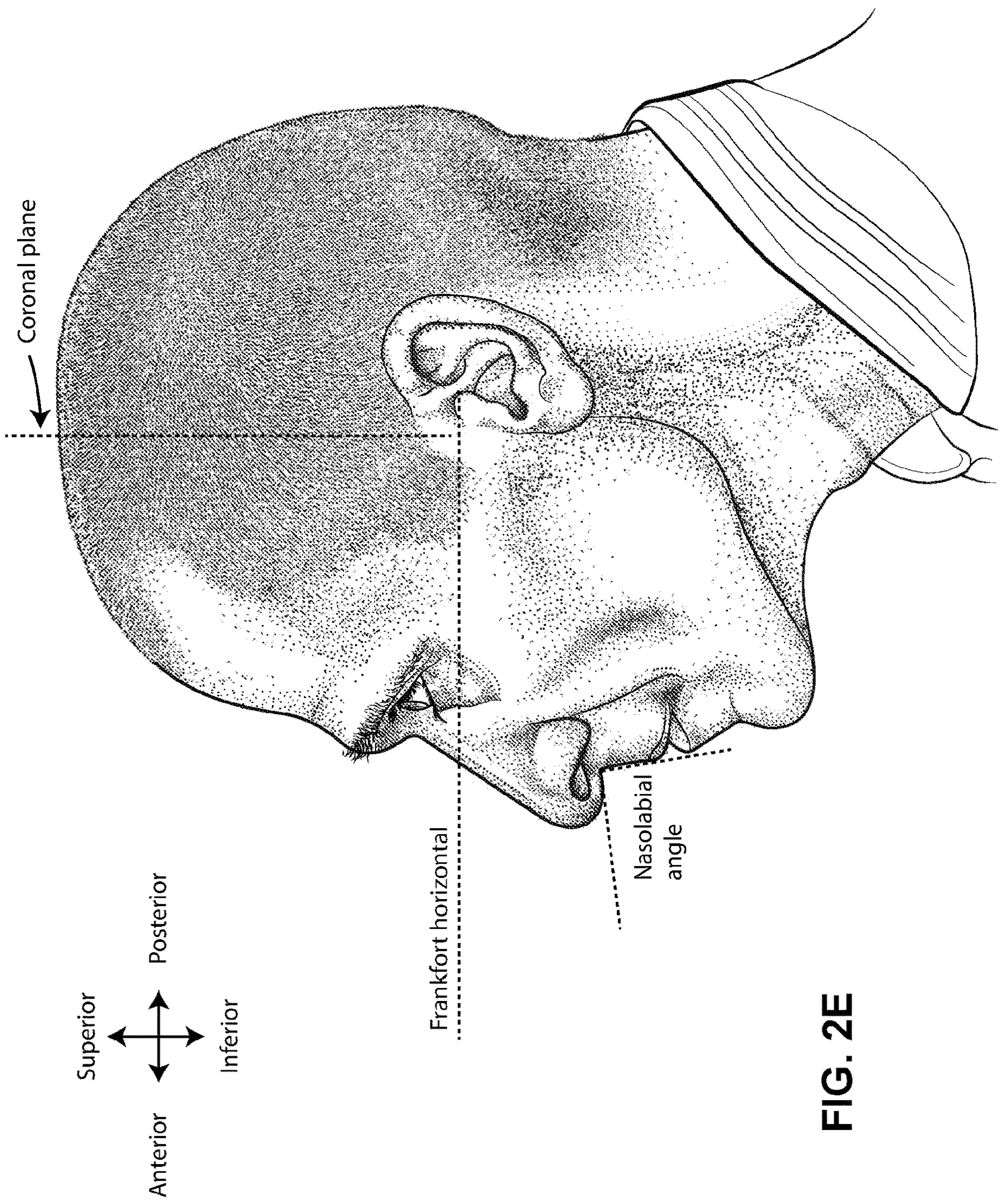

FIG. 2E is a further side view of a head. The approximate locations of the Frankfort horizontal and nasolabial angle are indicated. The coronal plane is also indicated.

Figure 2F:
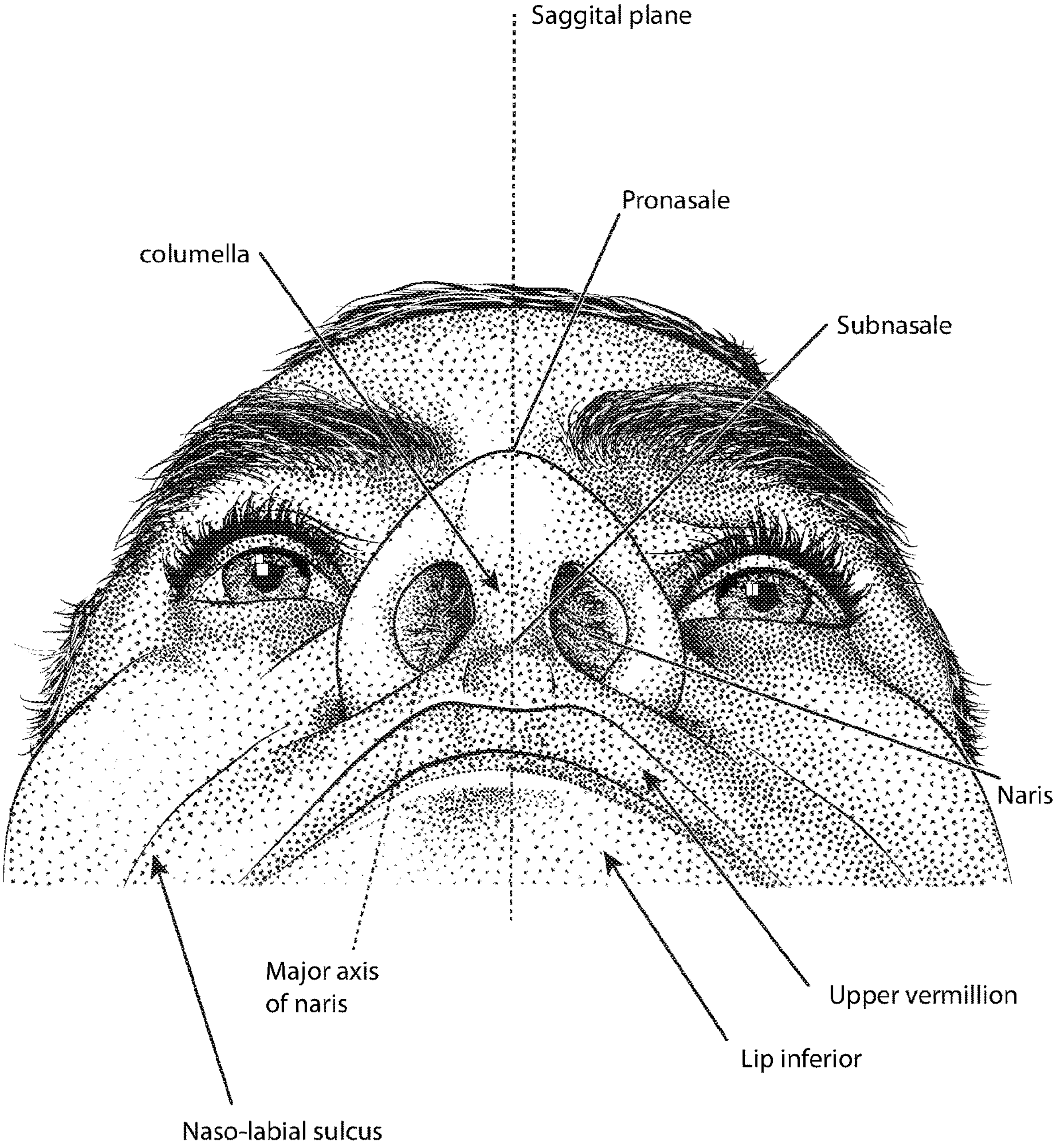

FIG. 2F shows a base view of a nose with several features identified including naso-labial sulcus, lip inferior, upper Vermilion, naris, subnasale, columella, pronasale, the major axis of a naris and the midsagittal plane.

Figure 2G:
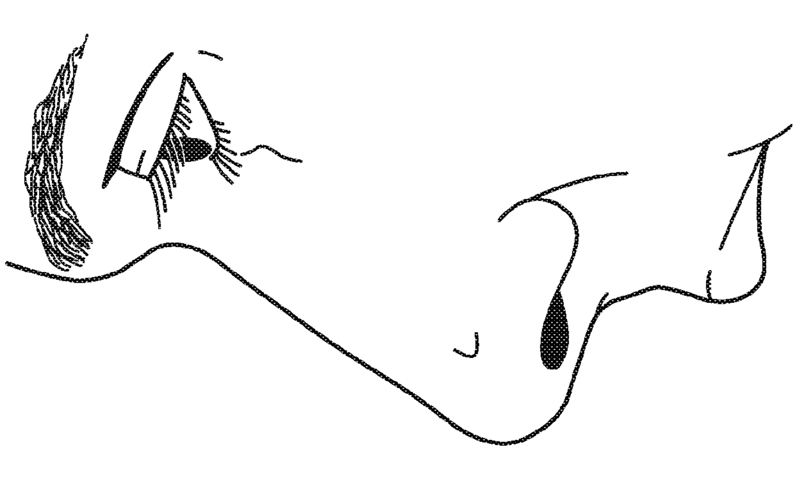

FIG. 2G shows a side view of the superficial features of a nose.

Figure 2H:
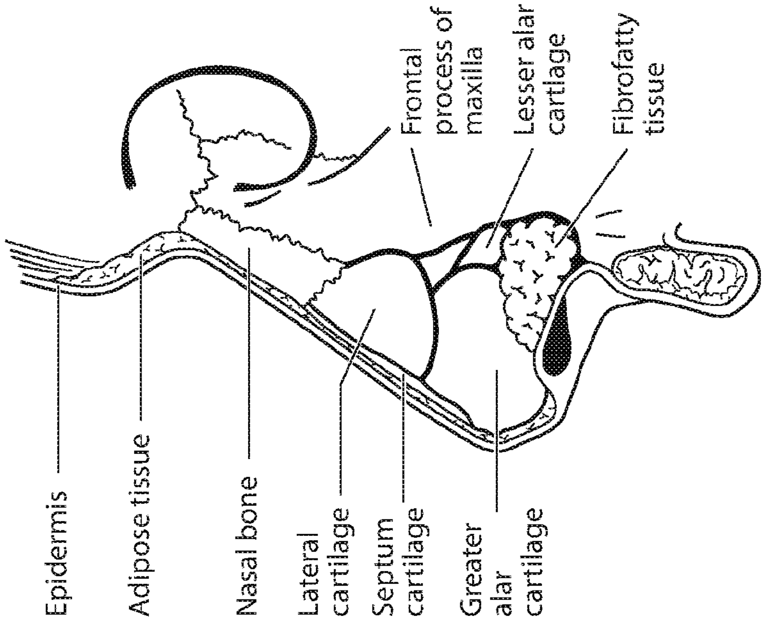

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

Figure 2I:
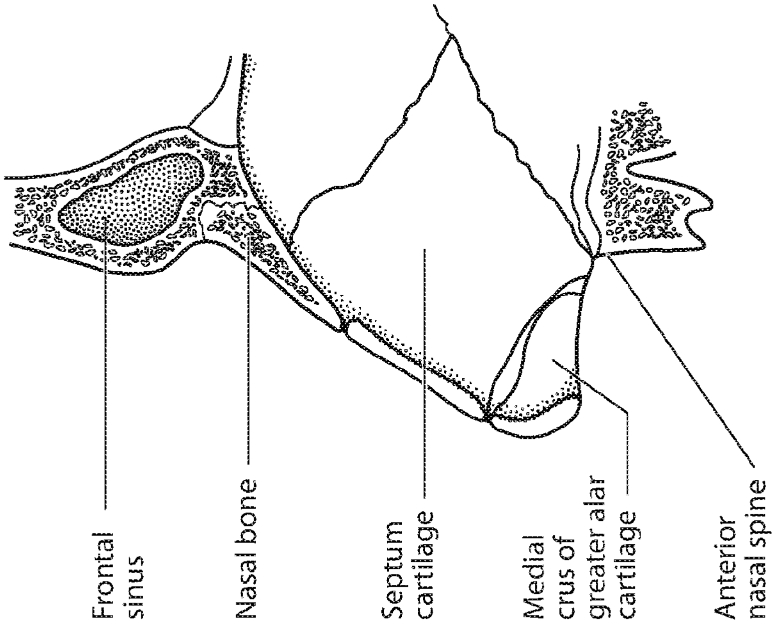

FIG. 2I shows a medial dissection of a nose, approximately several millimeters from the midsagittal plane, amongst other things showing the septum cartilage and medial crus of greater alar cartilage.

Figures 2J, 2K:
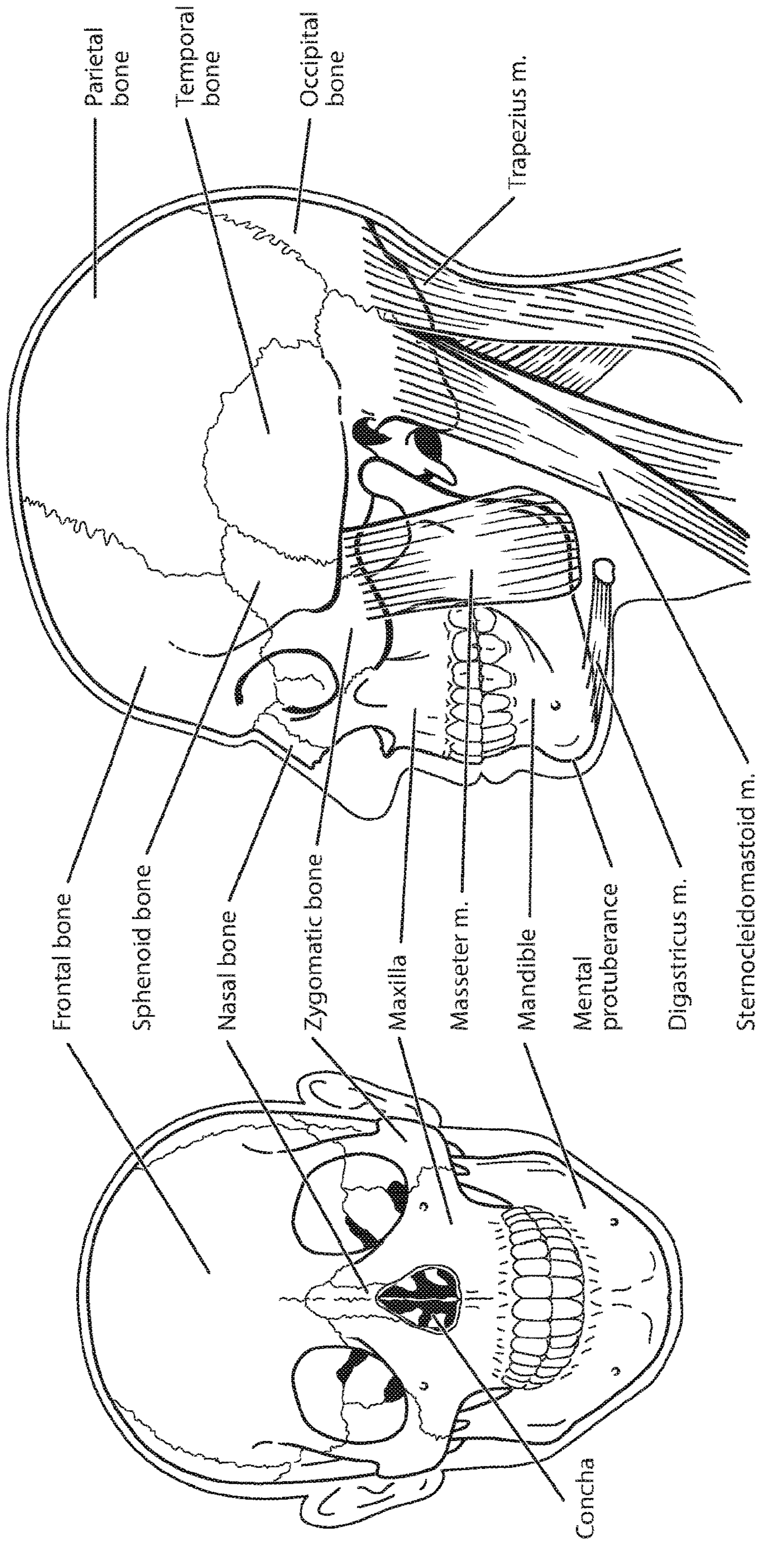

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
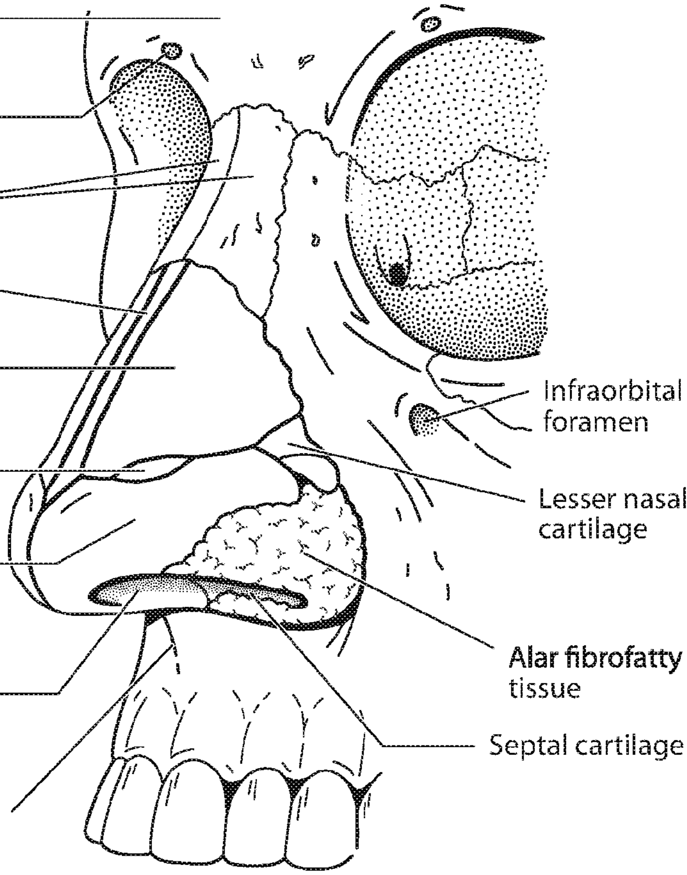

FIG. 2L shows an anterolateral view of a nose.

4.3 Patient Interface

Figure 3A:
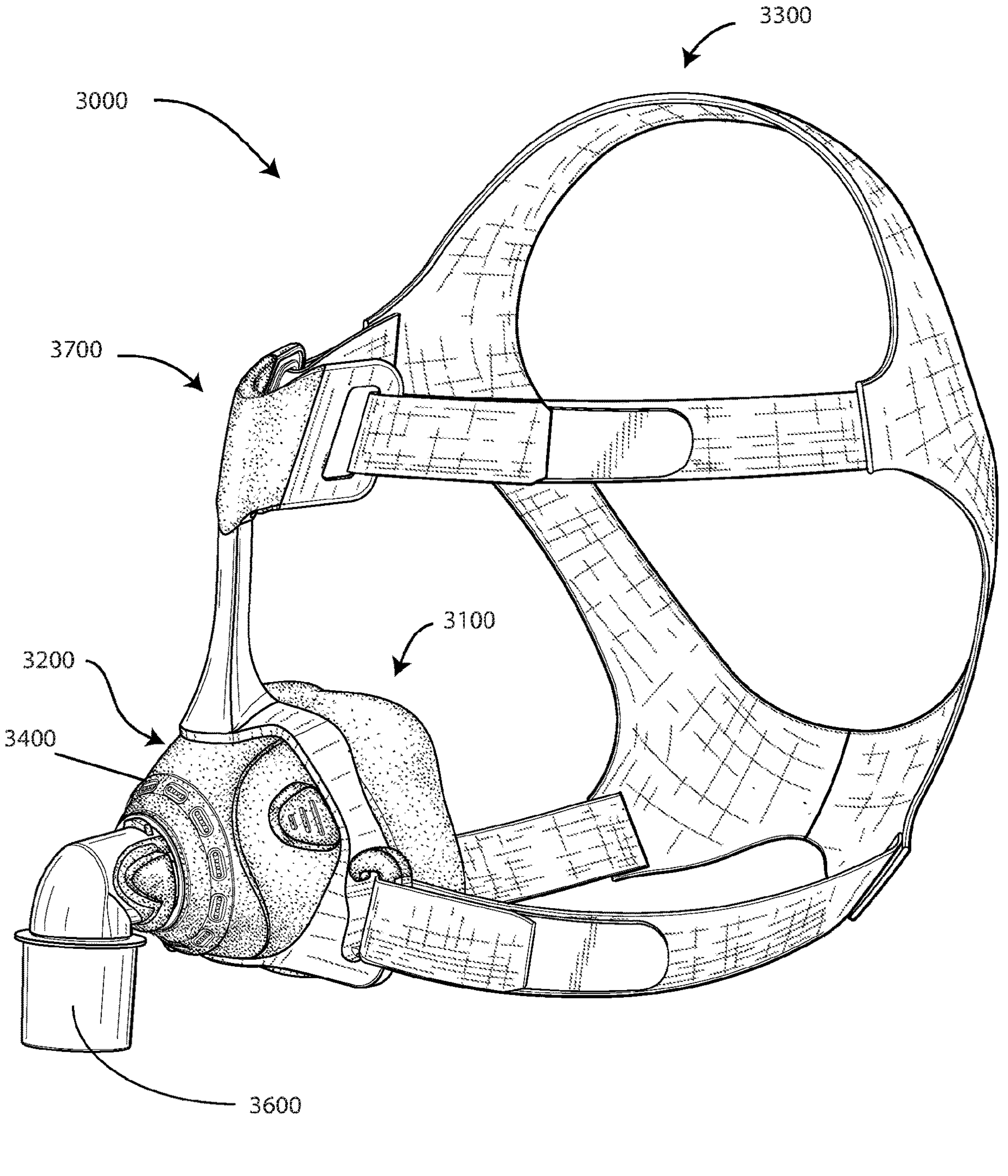

FIG. 3A shows a patient interface in the form of a nasal mask in accordance with one form of the present technology.

Figure 3B:
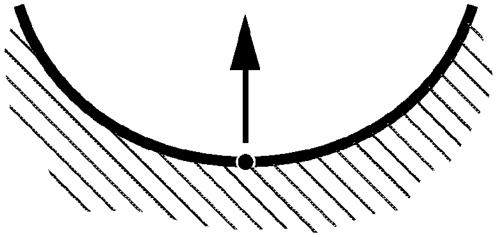

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
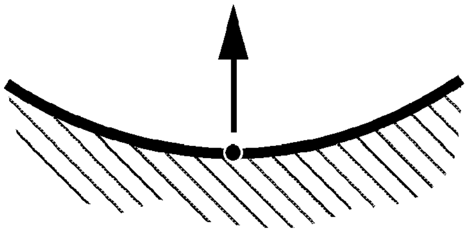

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
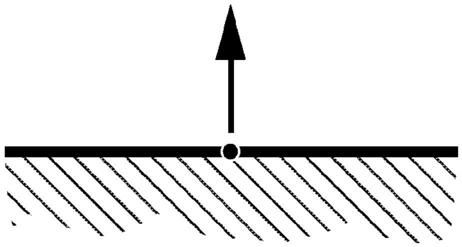

FIG. 3D shows a schematic of a cross-section through a structure at a point. An outward normal at the point is indicated. The curvature at the point has a value of zero.

Figure 3E:
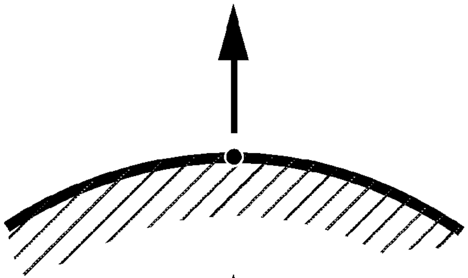

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
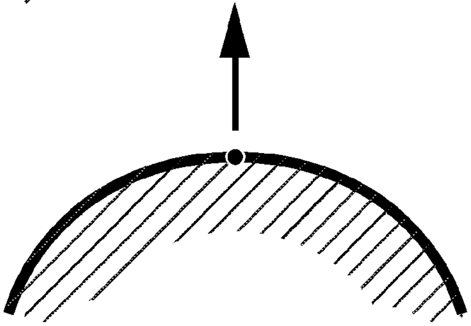

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
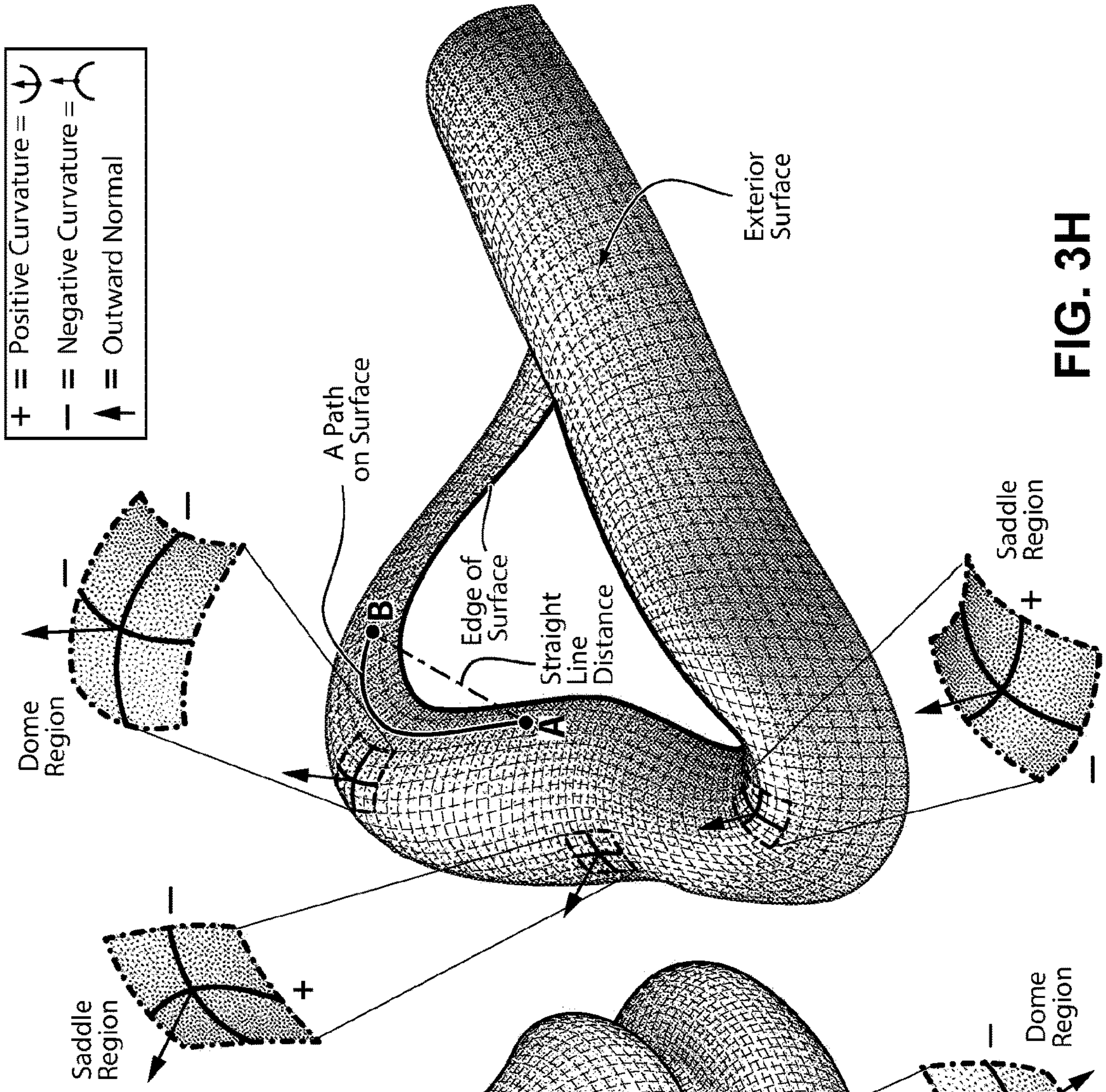
Figure 3G:
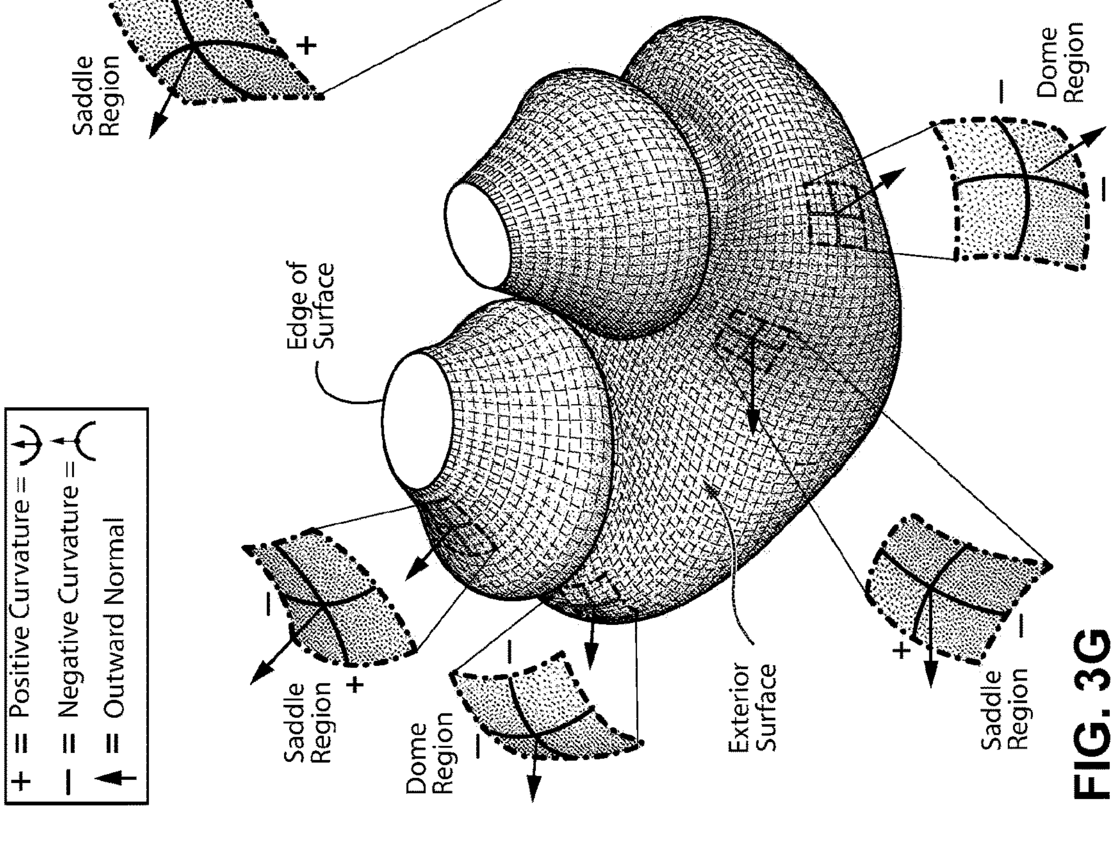

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
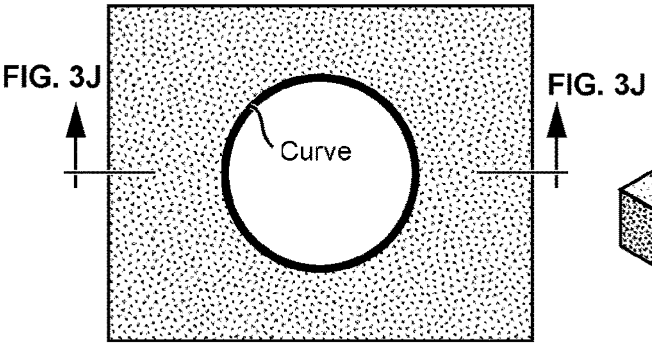

FIG. 3I shows the surface of a structure, with a one dimensional hole in the surface. The illustrated plane curve forms the boundary of a one dimensional hole.

Figure 3K:
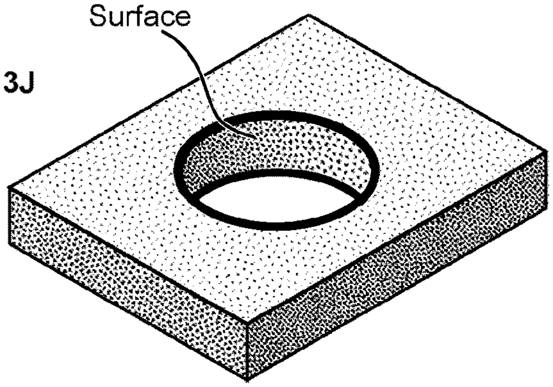
Figure 3J:
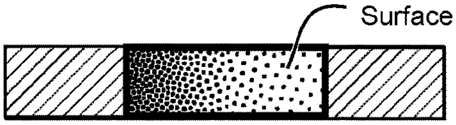

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
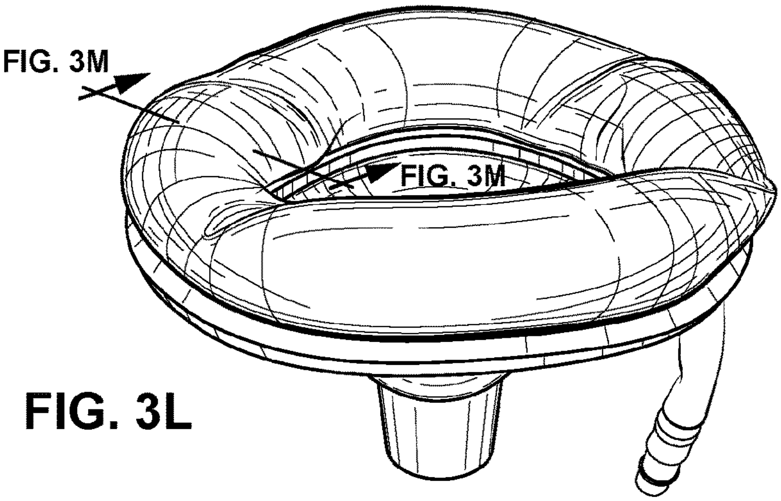

FIG. 3L shows a mask having an inflatable bladder as a cushion.

Figure 3M:
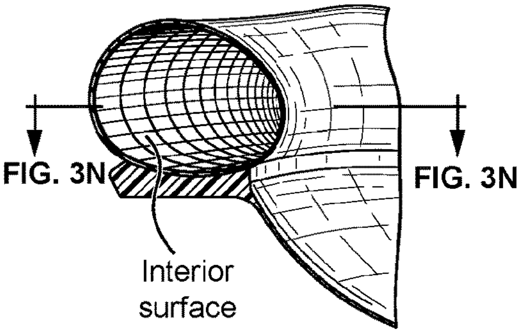

FIG. 3M shows a cross-section through the mask of FIG. 3L, and shows the interior surface of the bladder. The interior surface bounds the two dimensional hole in the mask.

Figure 3N:
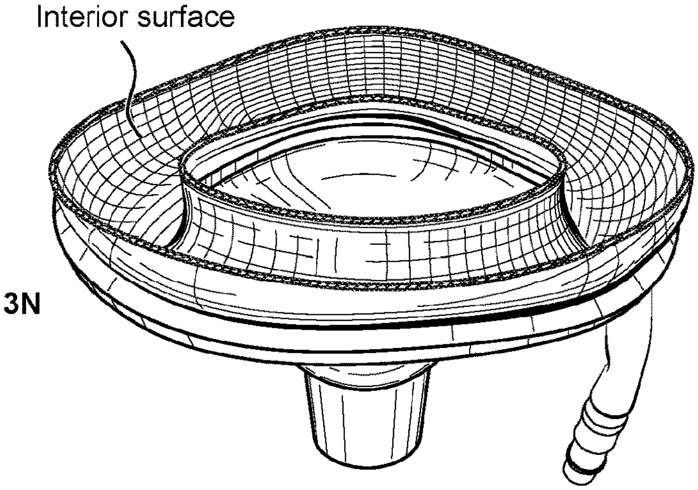

FIG. 3N shows a further cross-section through the mask of FIG. 3L. The interior surface is also indicated.

Figure 3O:
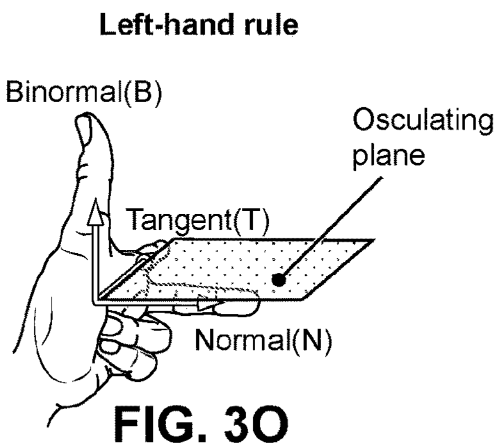

FIG. 3O illustrates a left-hand rule.

Figure 3P:
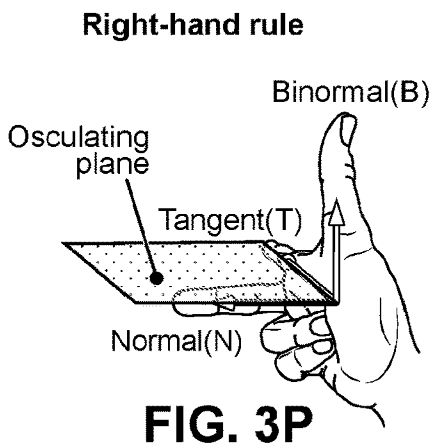

FIG. 3P illustrates a right-hand rule.

Figure 3Q:
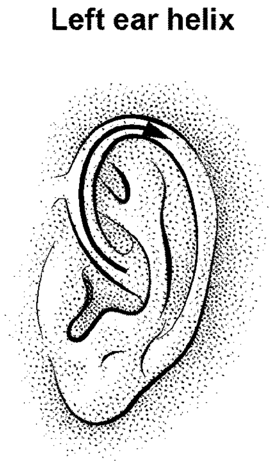

FIG. 3Q shows a left ear, including the left ear helix.

Figure 3S:
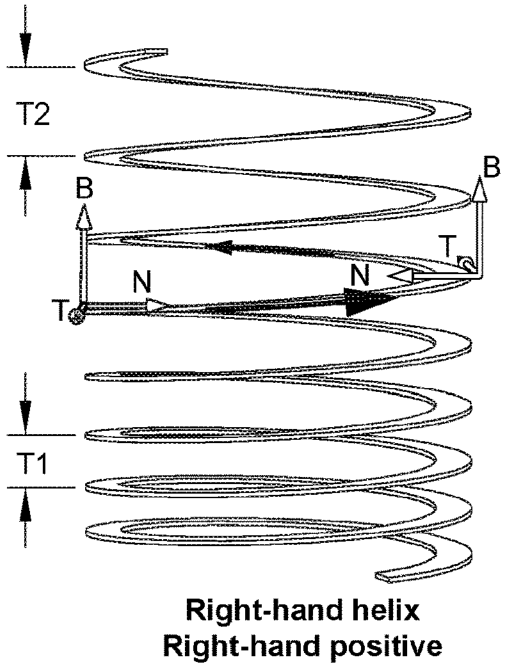
Figure 3R:
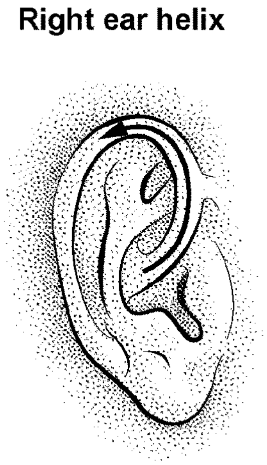

FIG. 3R shows a right ear, including the right ear helix.

FIG. 3S shows a right-hand helix.

Figure 3T:
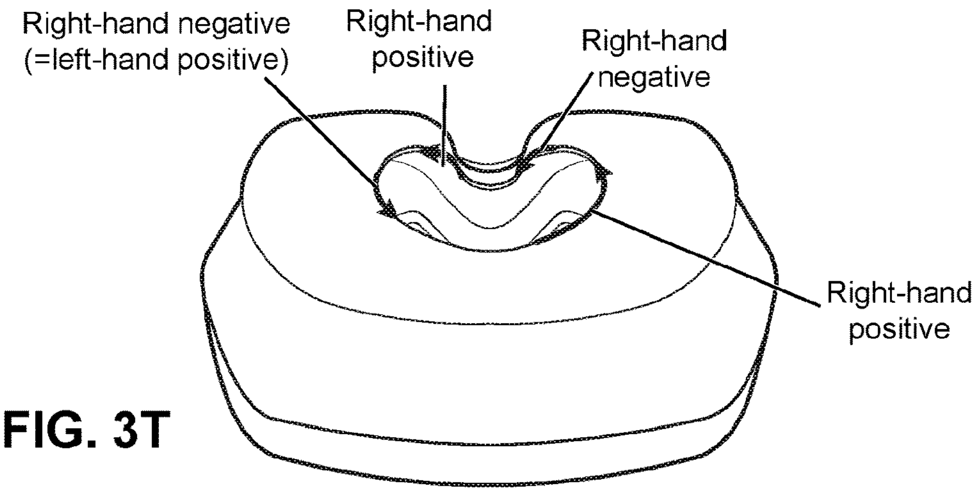

FIG. 3T shows a view of a mask, including the sign of the torsion of the space curve defined by the edge of the sealing membrane in different regions of the mask.

Figure 3U:
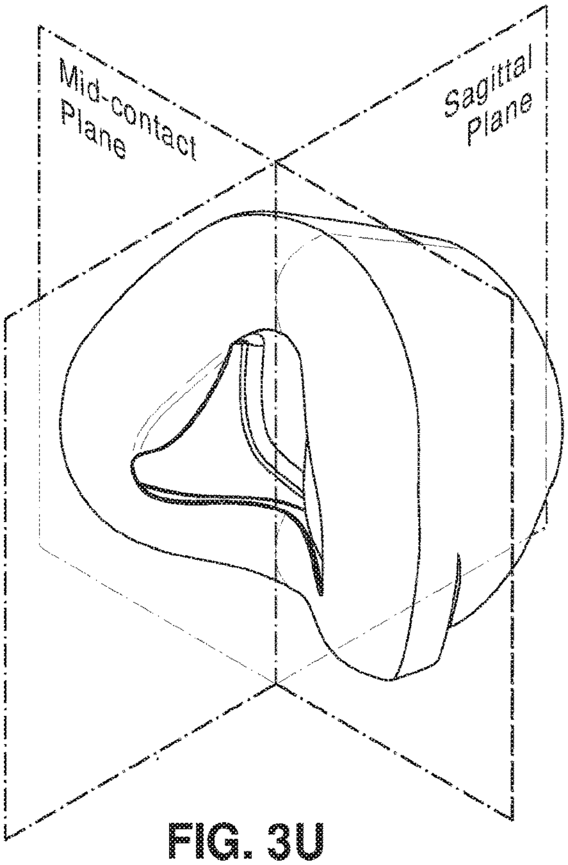

FIG. 3U shows a view of a plenum chamber 3200 showing a sagittal plane and a mid-contact plane.

Figure 3V:
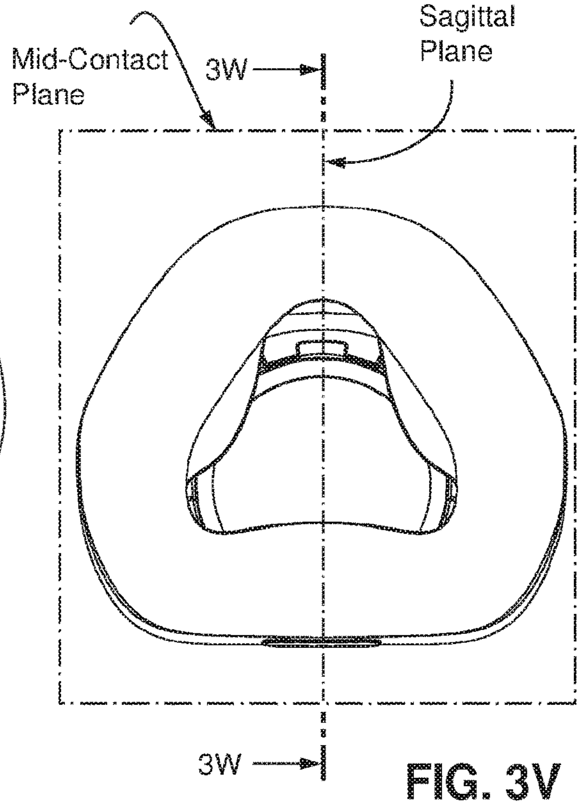

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
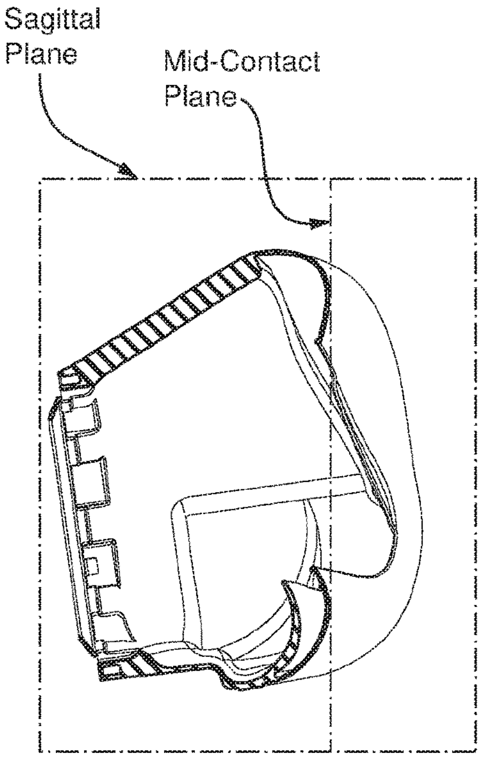

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
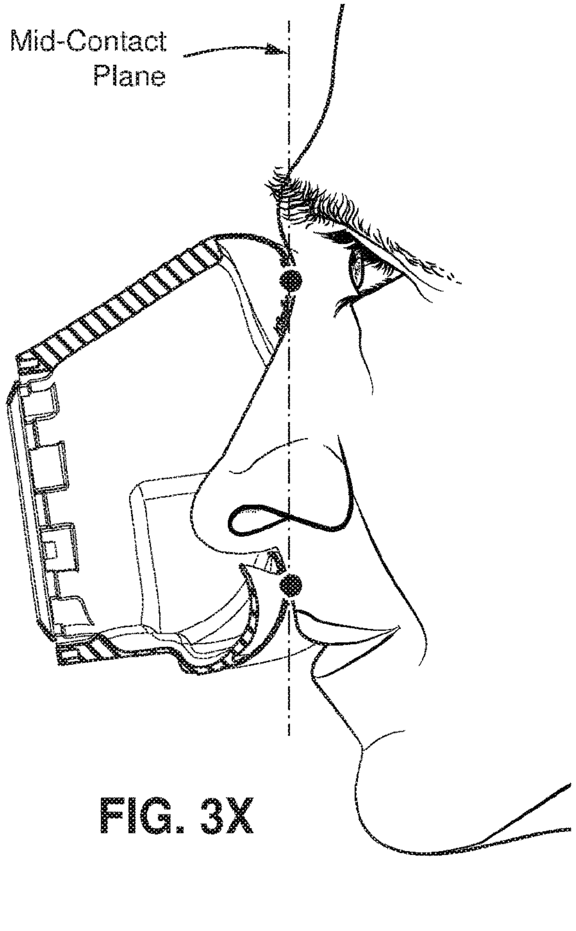

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 Patient Interface According to the Present Technology

Figure 4A:
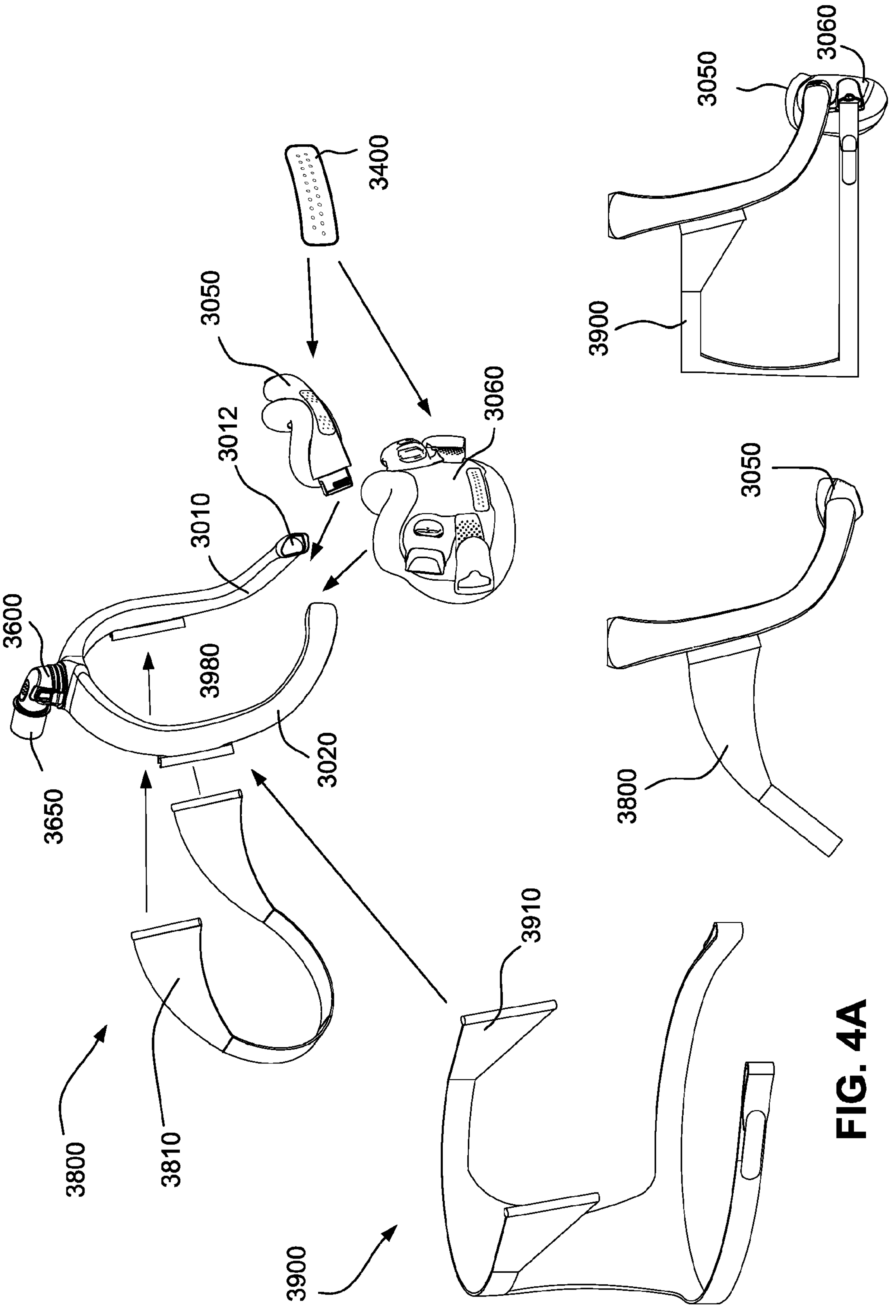

FIG. 4A shows a configurable patient interface according to an example of the present technology.

Figure 4B:
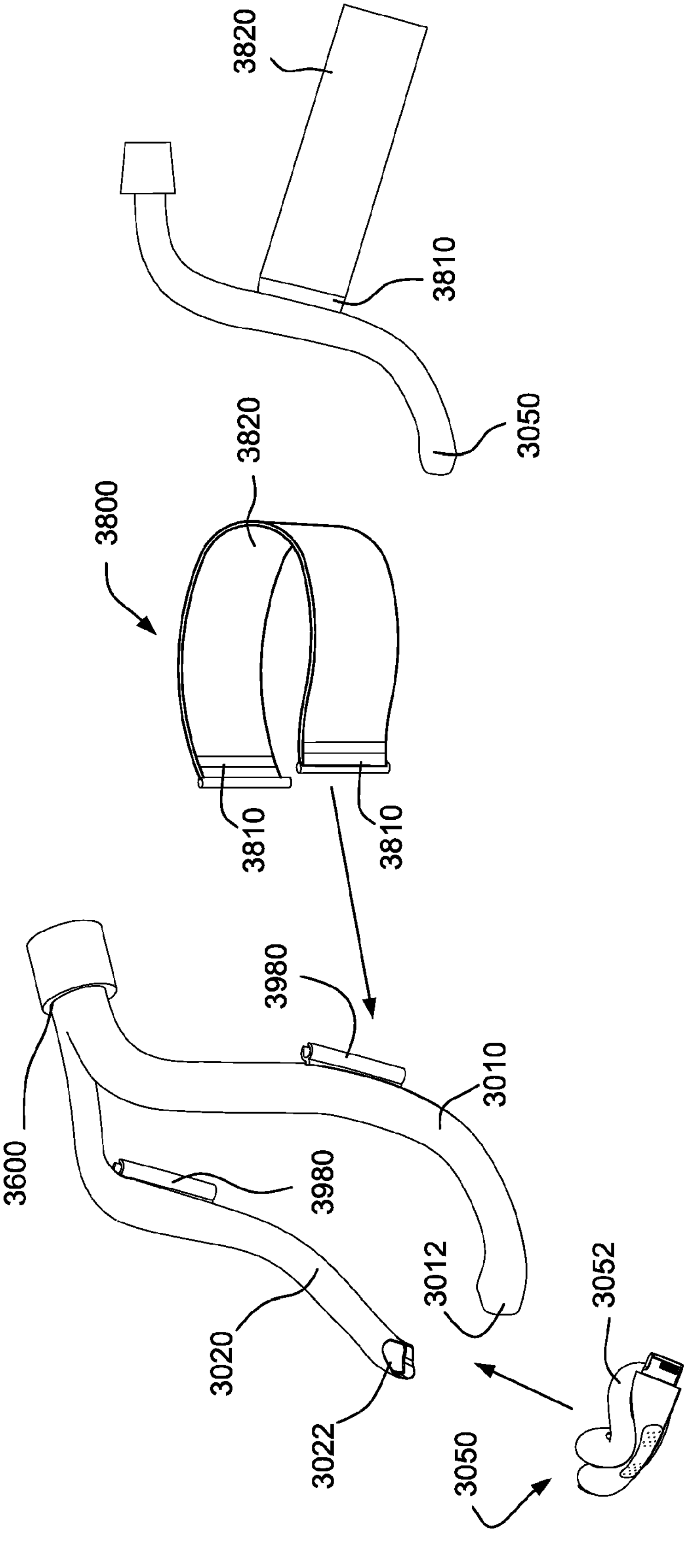

FIG. 4B shows a configurable patient interface in a nasal "under the nose" seal mask configuration according to an example of the present technology.

Figure 4C:
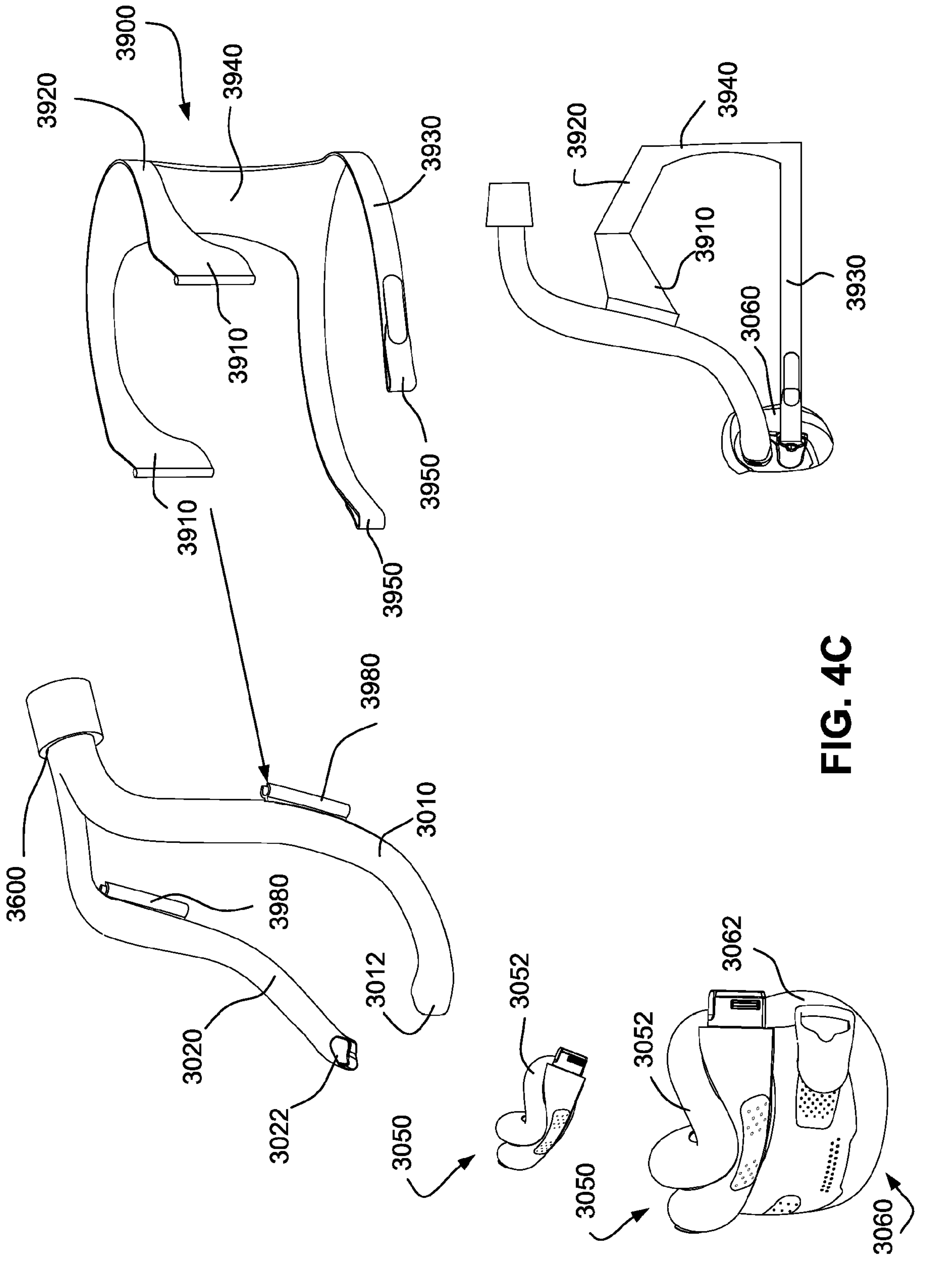

FIG. 4C shows a configurable patient interface in a convertible oro-nasal mask configuration according to another example of the present technology.

Figure 5A:
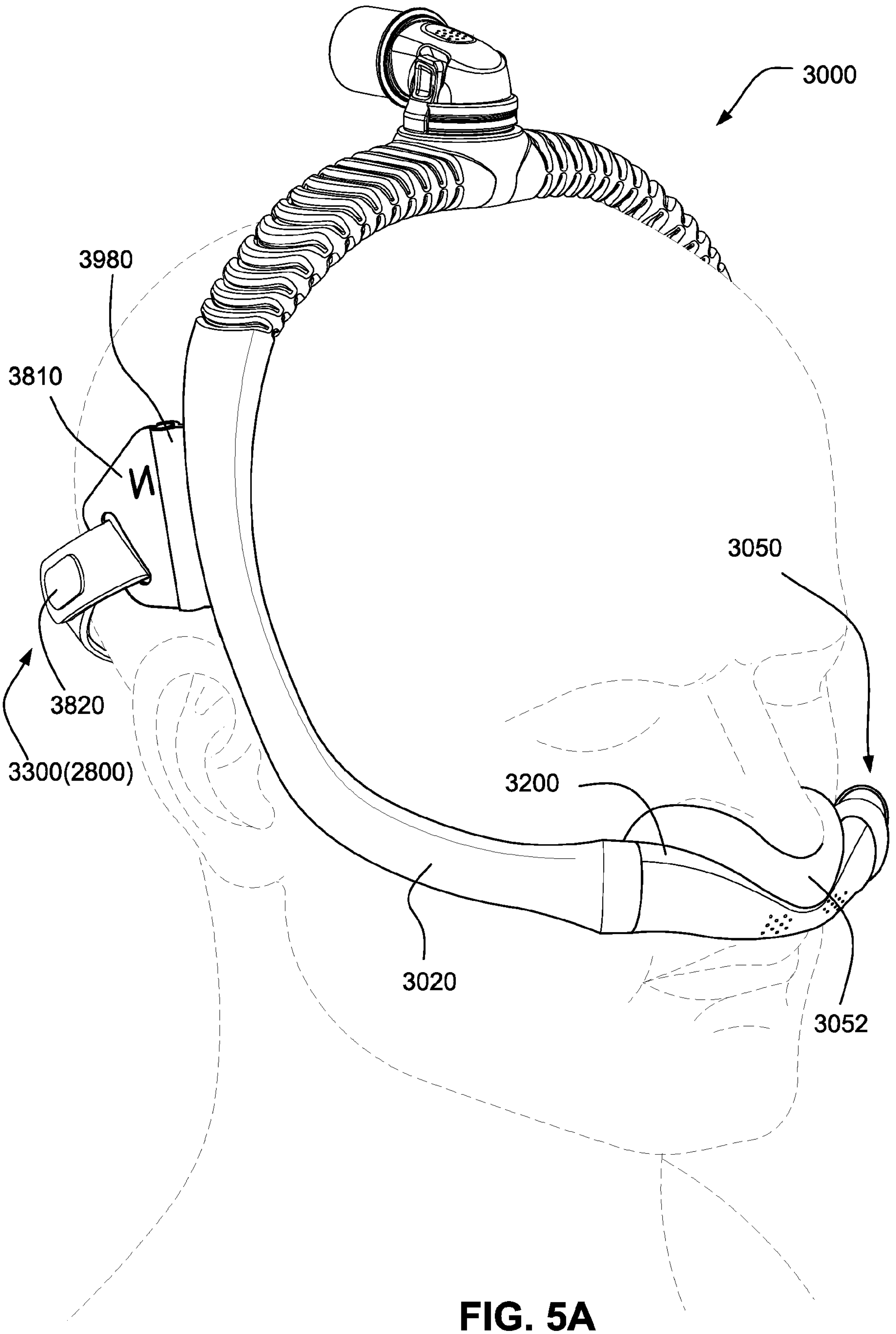

FIG. 5A shows a perspective view of a patient interface configured in a nasal configuration according to an example of the present technology.

Figure 5B:
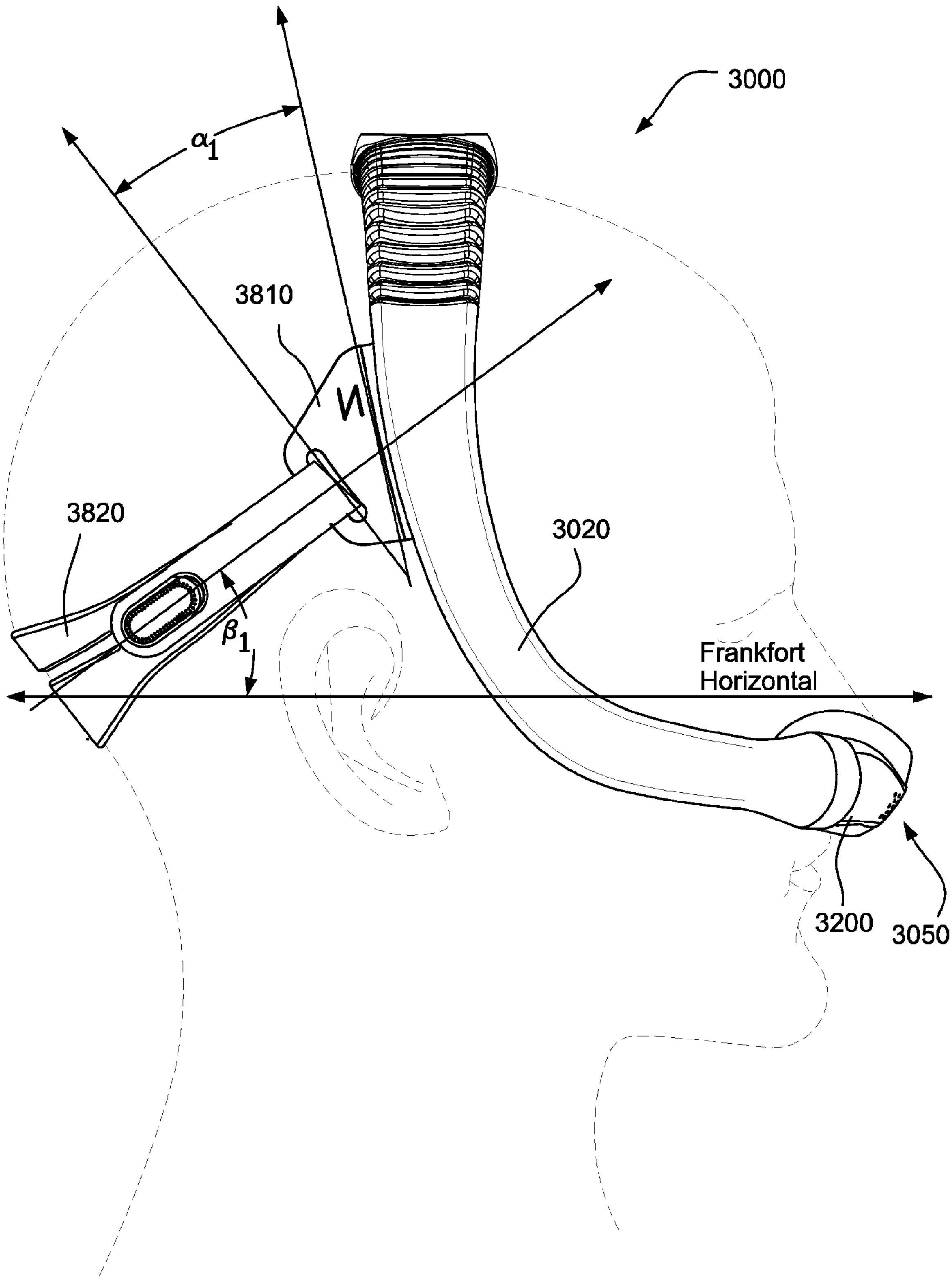

FIG. 5B shows a side view of a patient interface configured in the nasal configuration according to an example of the present technology.

Figure 5C:
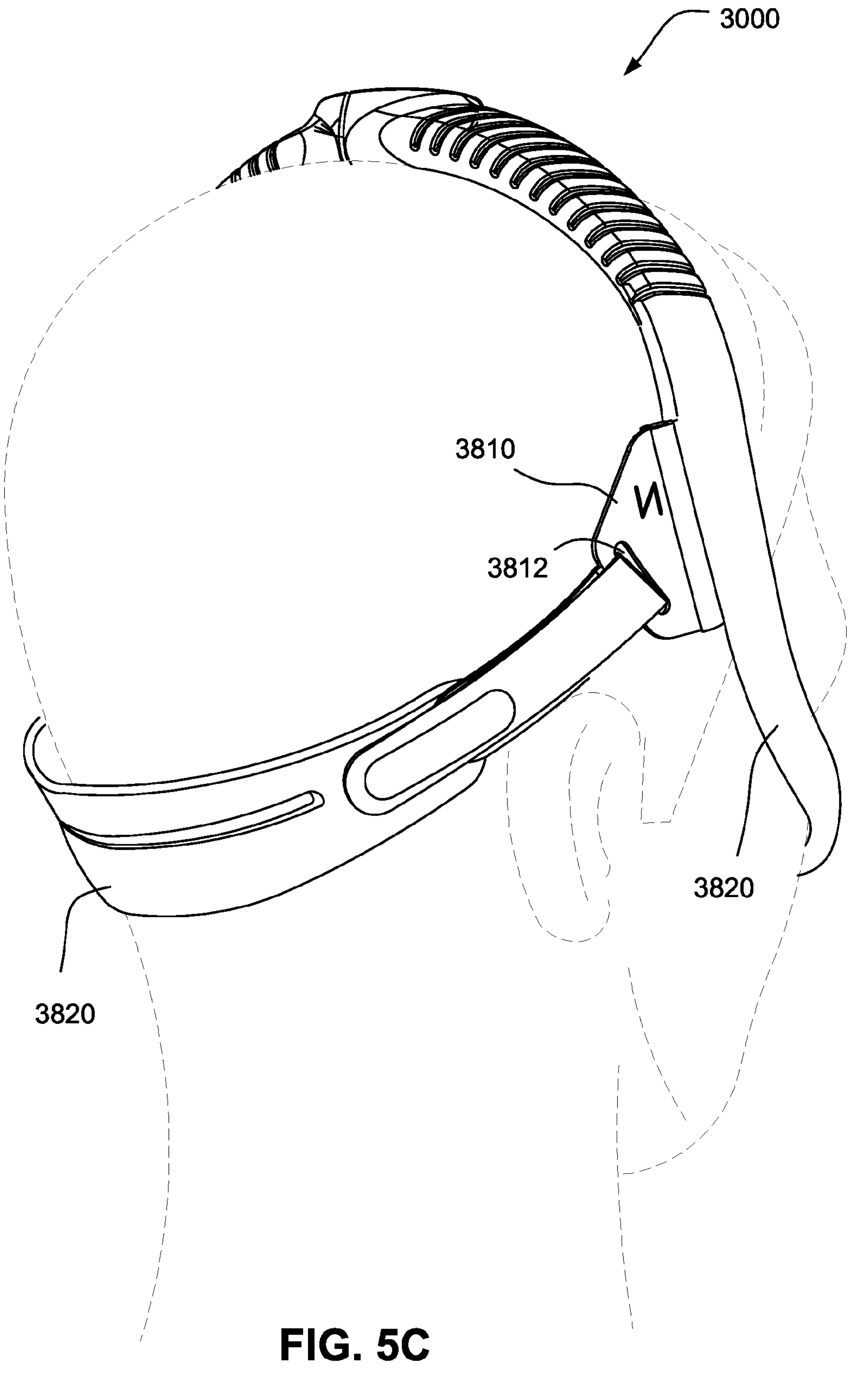

FIG. 5C shows a back view of a patient interface configured in the nasal configuration according to an example of the present technology.

Figure 5D:
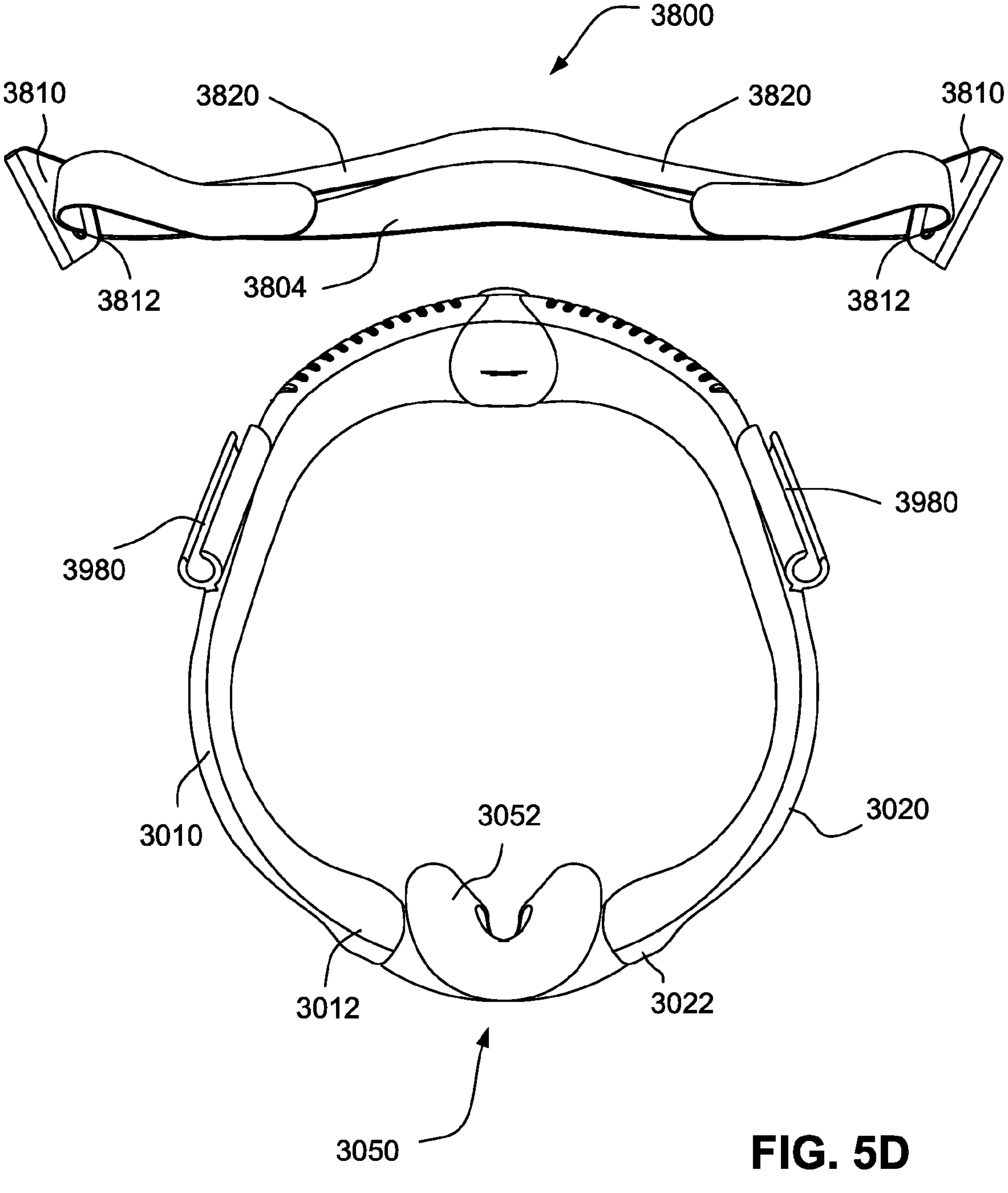

FIG. 5D shows disassembled patient interface of the nasal configuration according to an example of the present technology.

Figure 6A:
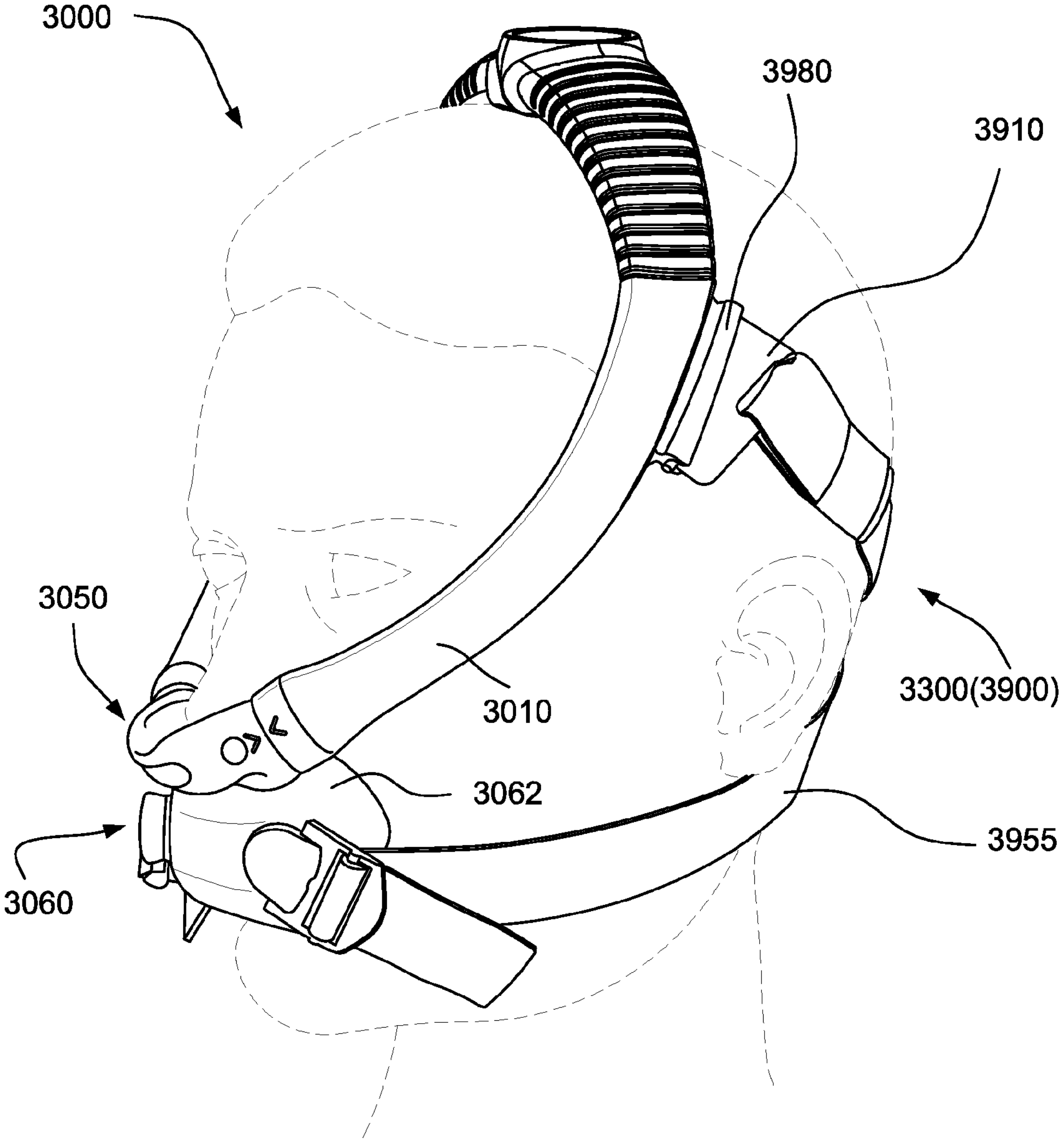

FIG. 6A shows a perspective view of a patient interface configured in an oro-nasal configuration according to an example of the present technology.

Figure 6B:
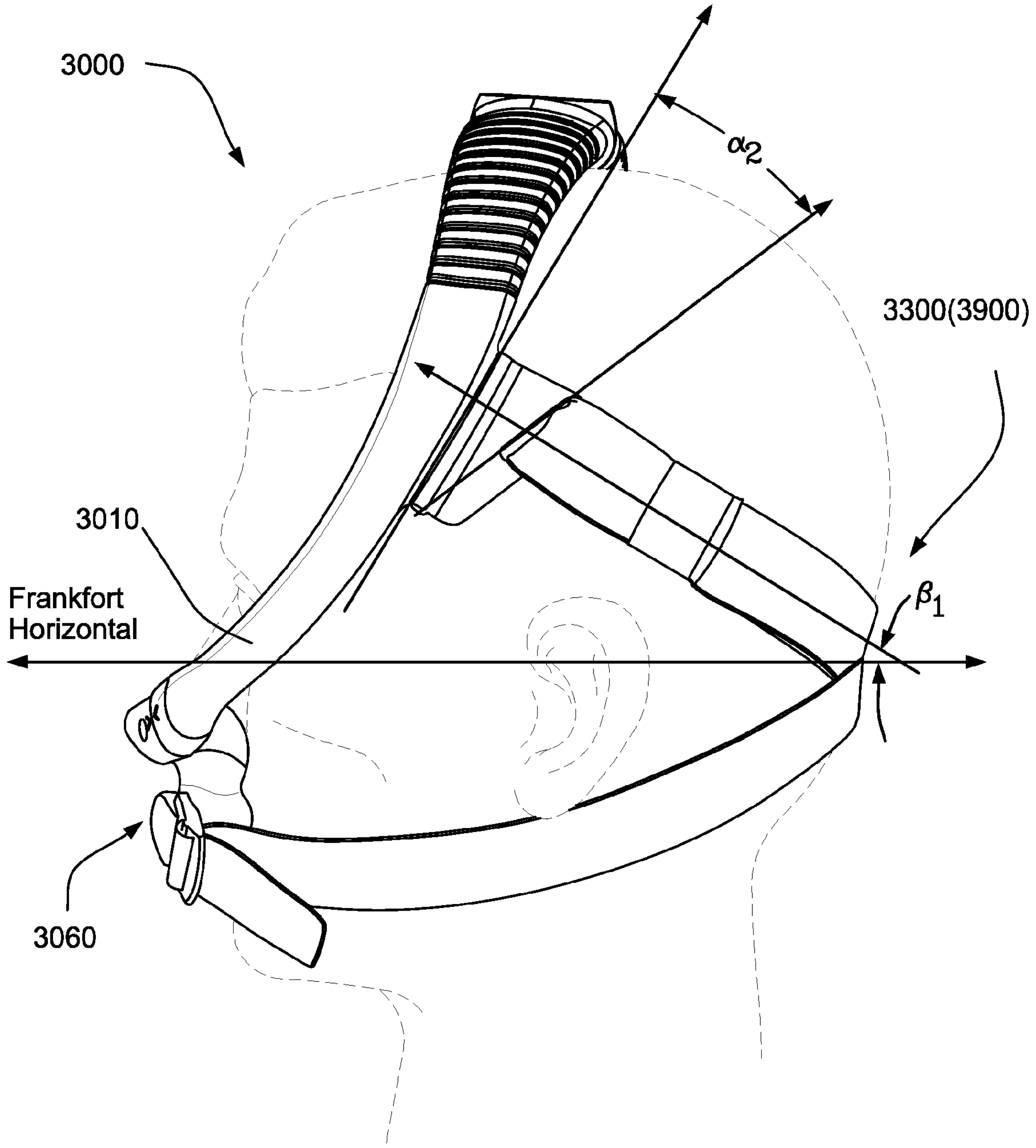

FIG. 6B shows a side view of a patient interface configured in the oro-nasal configuration according to an example of the present technology.

Figure 6C:
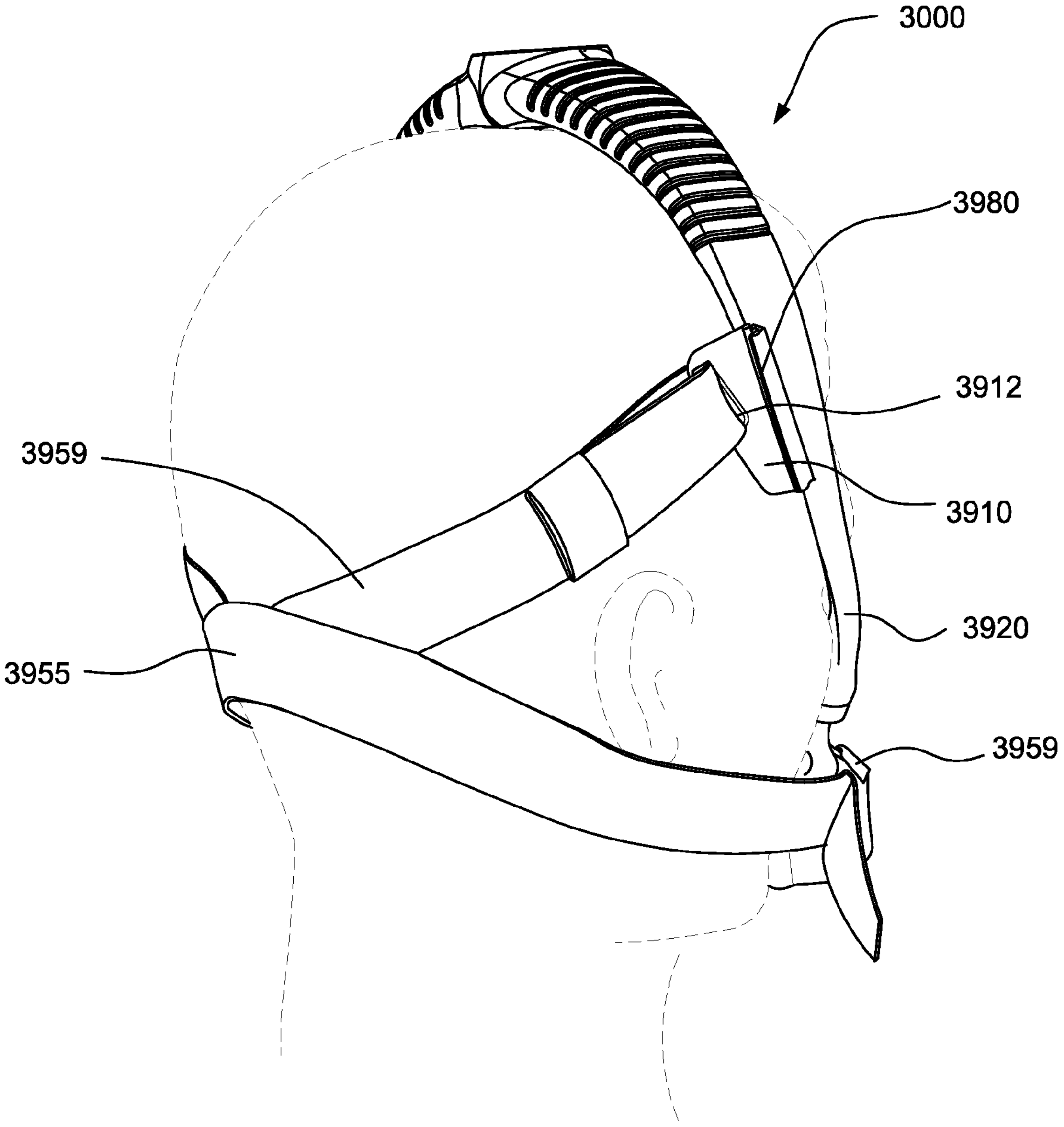

FIG. 6C shows a back view of a patient interface configured in the oro-nasal configuration according to an example of the present technology.

Figure 6D:
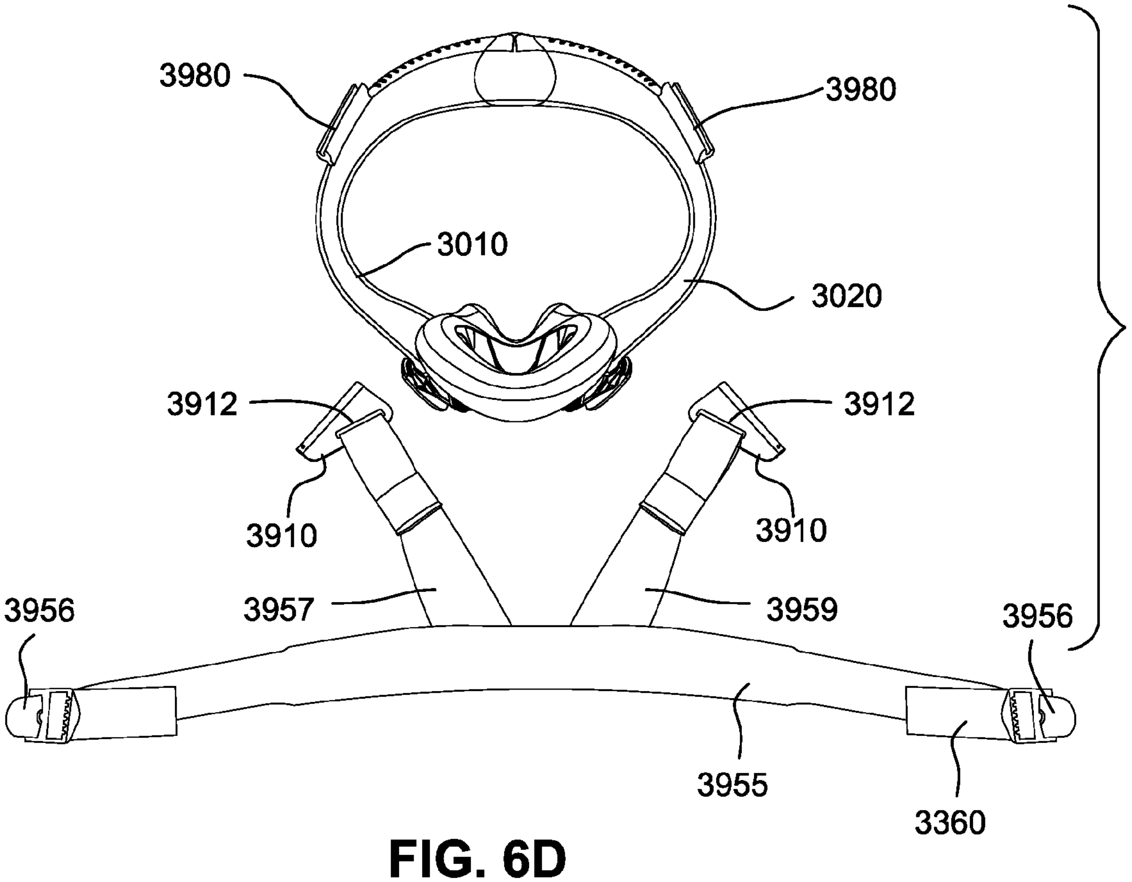

FIG. 6D shows disassembled patient interface of the oro-nasal configuration according to an example of the present technology.

Figure 7A:
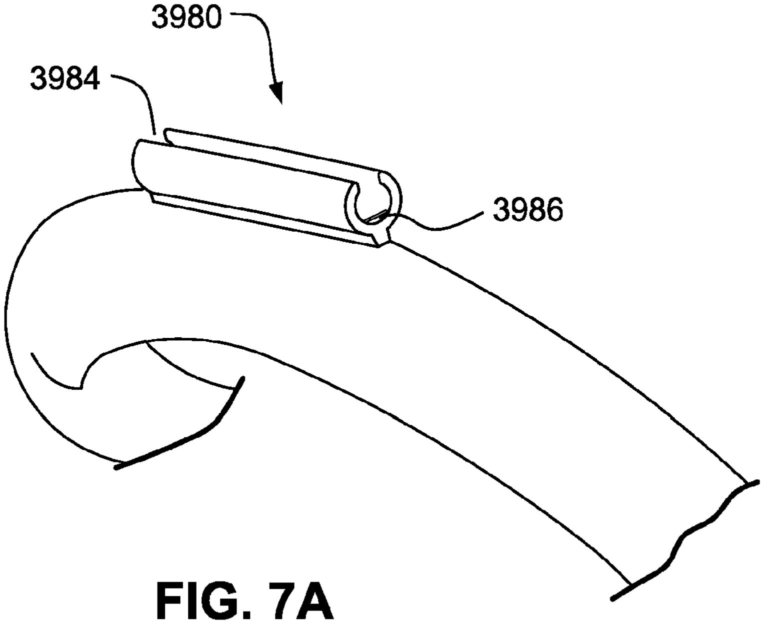

FIG. 7A shows a first view of a common connecting element provided on a headgear section according to an example of the present technology.

Figure 7B:
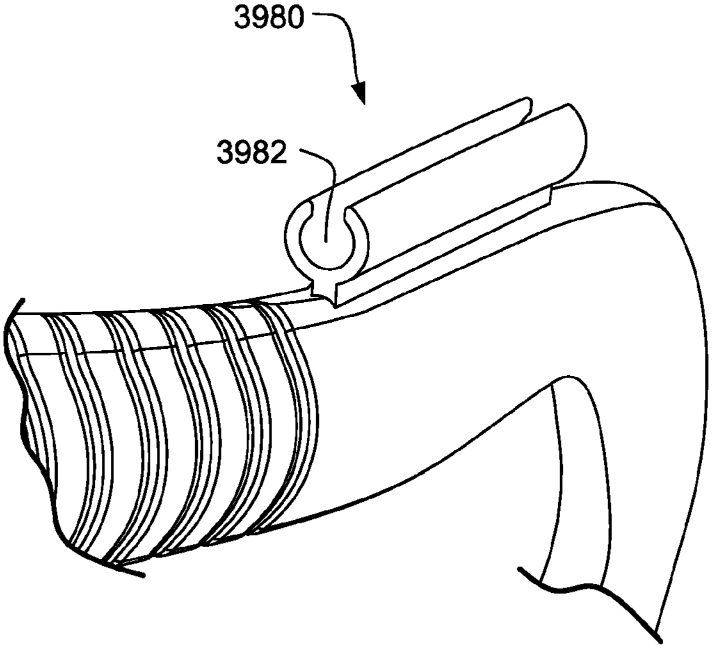

FIG. 7B shows a second view of a common connecting element provided on a headgear section according to an example of the present technology.

Figure 7C:
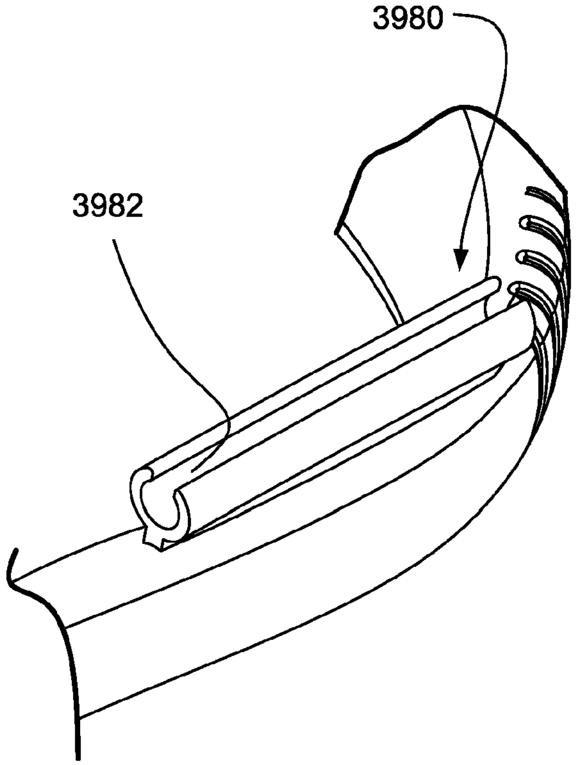

FIG. 7C shows a third view of a common connecting element provided on a headgear section according to an example of the present technology.

Figure 7D:
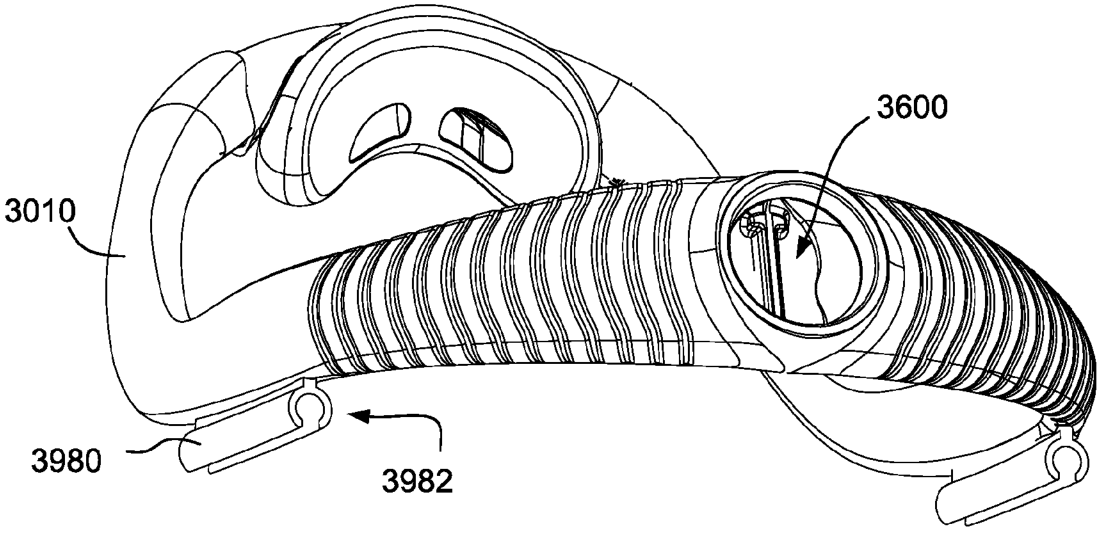

FIG. 7D shows a fourth view of a common connecting element provided on a headgear section according to an example of the present technology.

Figure 7E:
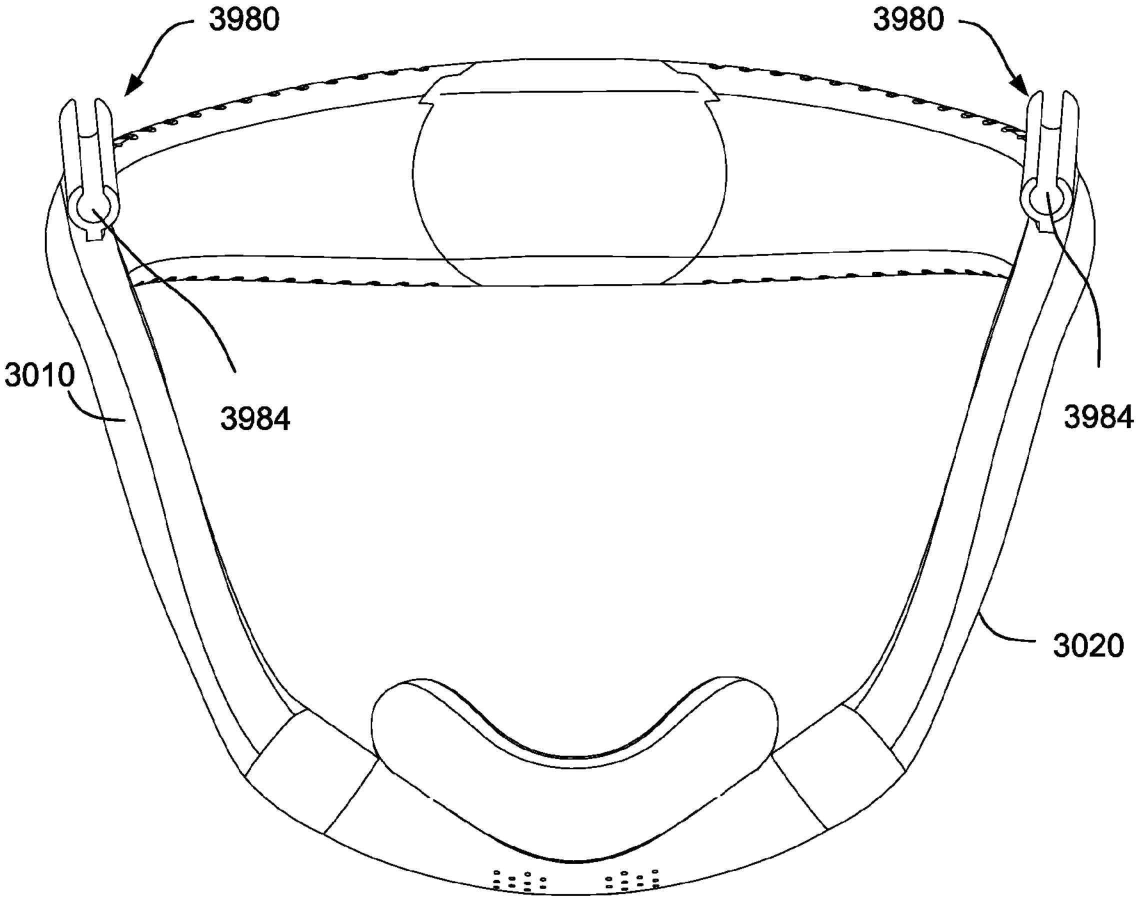

FIG. 7E shows a two common connecting elements provided on a respective headgear sections according to an example of the present technology.

Figure 8:
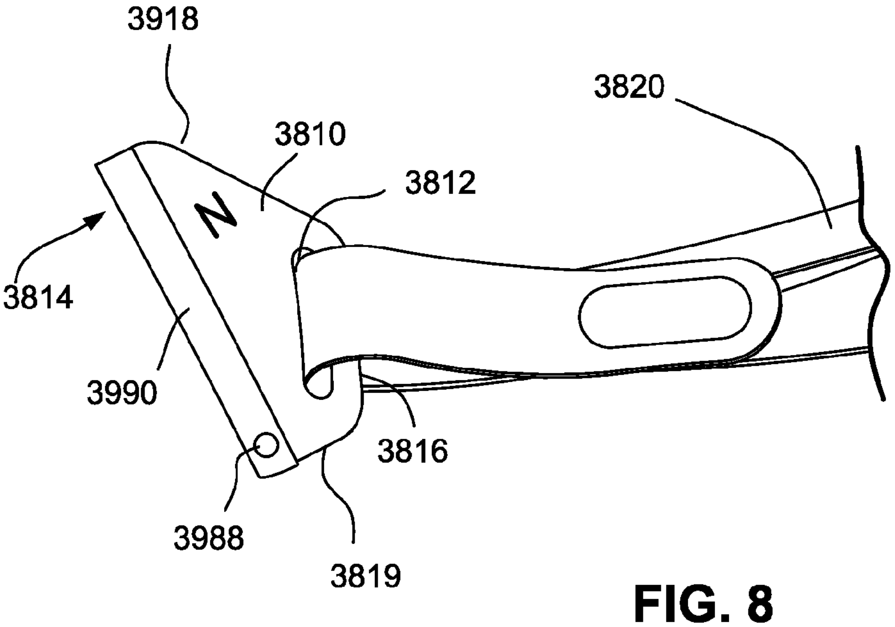

FIG. 8 shows a nasal headgear clips according to an example of the present technology.

Figure 9:
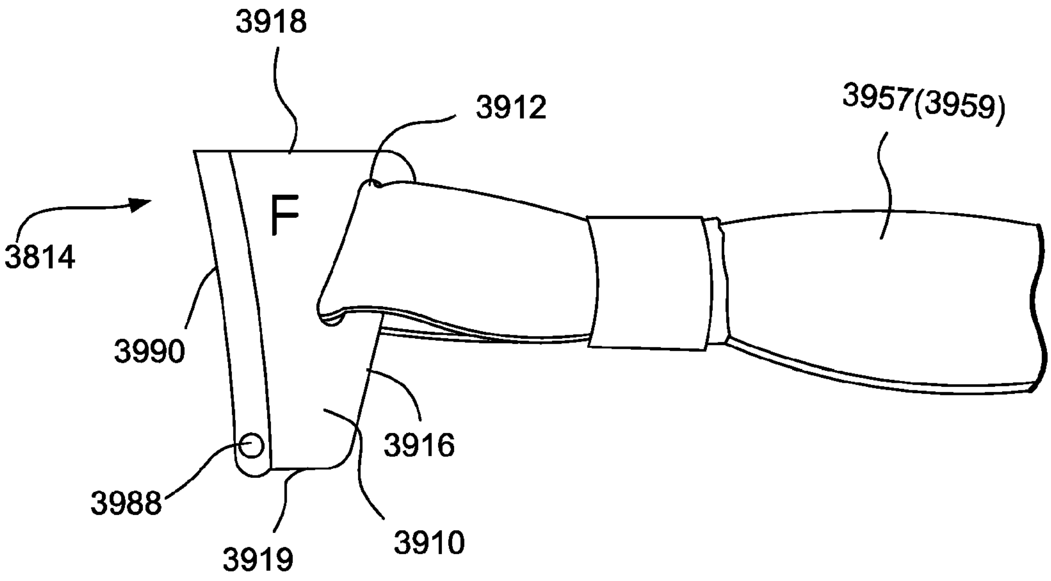

FIG. 9 shows an oro-nasal headgear clips according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1A:
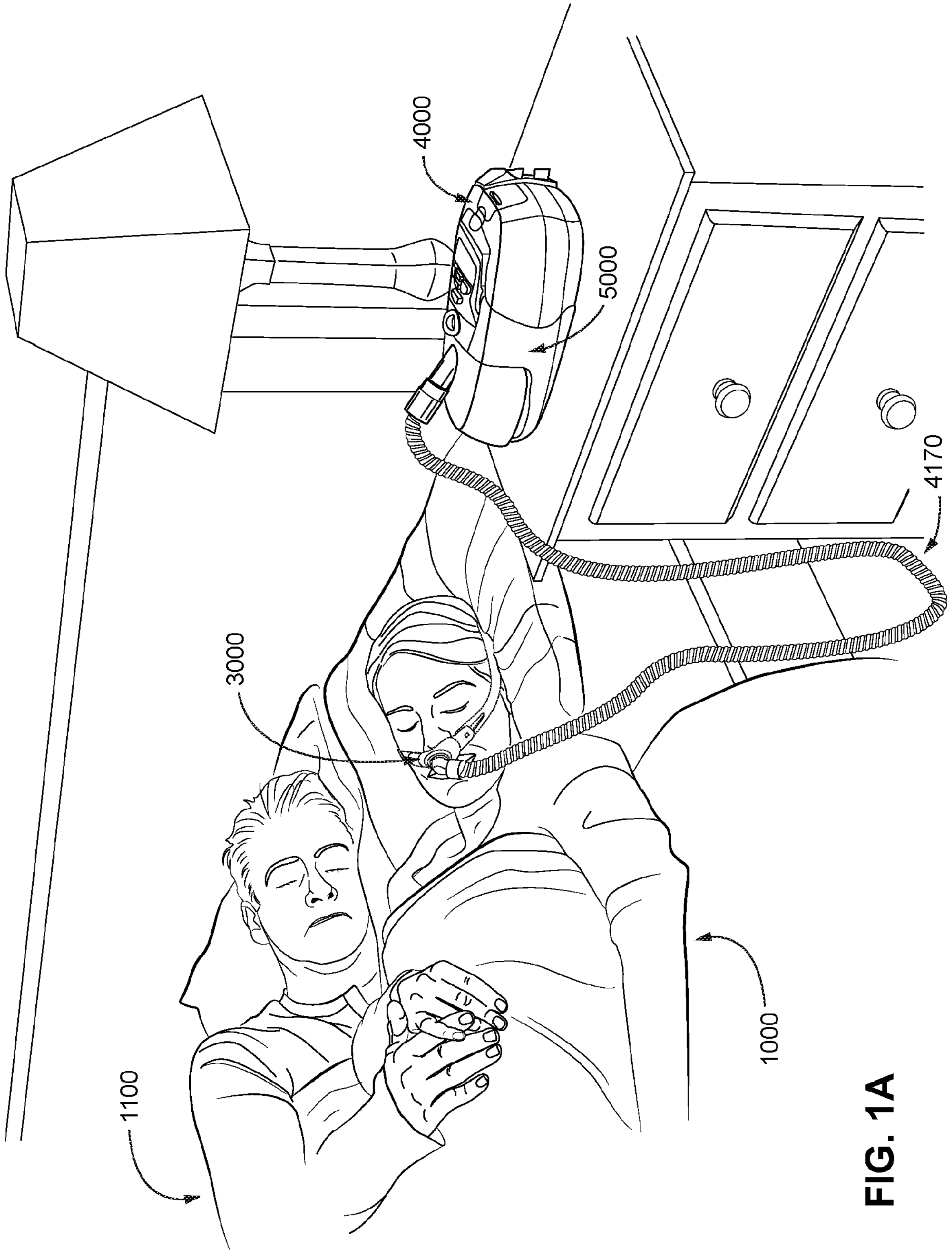
Figure 1B:
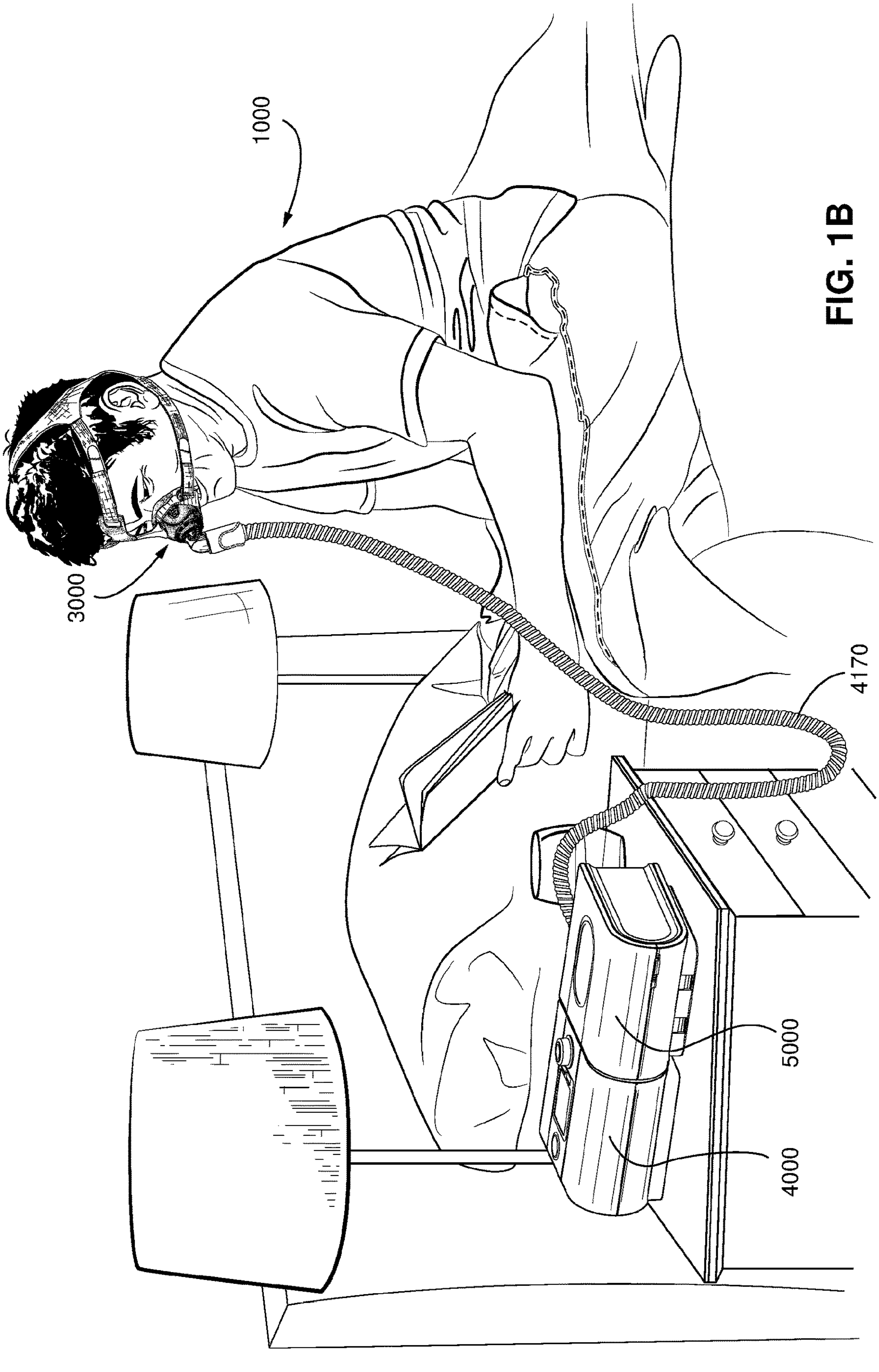
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

Referring to FIGS. 4A to 9, a non-invasive patient interface 3000 in accordance with one aspect of the present technology to deliver a flow of air at a positive pressure with respect to ambient air pressure to an entrance to a patient's airways. The patient interface 3000 comprises a positioning and stabilizing structure 3300, including a first headgear section 3010 (e.g., a left headgear section) and a second headgear section 3020 (e.g., right headgear section), each adapted to pass along a patient's cheek under a patient's eye and between the patient's eye and ear. The positioning and stabilizing structure 3300 may include a nasal headgear 3800 or an oro-nasal headgear 3900.

The patient interface 3000 may be convertible between a nasal "under the nose" seal mask and an oro-nasal mask, depending on whether a nasal cushion 3050 and/or a mouth cushion 3060 is/are coupled to the first and second headgear sections. The first headgear section 3010 may include a left common cushion interface 3012 and the second headgear section 3020 may include a right common cushion interface 3022 for coupling to the nasal cushion 3050 and/or the mouth cushion 3060. The nasal cushion 3050 comprises a nasal seal forming structure 3052 constructed and arranged to form a seal with a region of a patient's face surrounding the entrance to a patient's nares. The mouth cushion 3060 comprises a mouth seal-forming structure 3062 constructed and arranged to form a seal with a region of a patient's face surrounding the entrance to a patient's mouth.

In some forms, a functional aspect may be provided by one or more physical components. In some forms, one physical component may provide one or more functional aspects. In use the nasal seal-forming structure 3052 and/or the mouth seal-forming structure 3062 are arranged to surround an entrance to the airways of the patient so as to facilitate the supply of air at positive pressure to the airways.

In the illustrated example, the patient interface 3000 includes a connection port or opening 3600 for connection to the air circuit 4170. The patient interface 3000 may include a crown piece connecting the left and right headgear sections, the crown piece including an opening that receives a rotatable elbow 3650. The connection port rotatable elbow 3650 is adapted to connect to the air circuit 4170. As illustrated in FIG. 4B, the first headgear section 3010 and the second headgear section 3020 may be joined by the connection port 3600.

The nasal cushion 3050 and/or the mouth cushion 3060 form at least part of a plenum chamber 3200 pressurizable to a therapeutic pressure. The plenum chamber 3200 may receive a flow of pressurised gas from the air circuit 4170, which may pass through the nasal seal forming structure 3052 and/or the mouth seal-forming structure 3062 and into the patient's airways for inhalation.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Seal-Forming Structure

In one form of the present technology, a seal-forming structure, which may be a nasal seal-forming structure 3052 or a mouth seal-forming structure 3062, provides a target seal-forming region, and may additionally provide a cushioning function. The target seal-forming region is a region on the nasal seal forming structure 3052 or the mouth seal-forming structure 3062 where sealing may occur. The region where sealing actually occurs—the actual sealing surface—may depend on whether the nasal cushion 3050 or the mouth cushion 3060 is being used and may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the nasal seal forming structure 3052 and/or the mouth seal-forming structure 3062.

In certain forms of the present technology, the nasal seal forming structure 3052 and/or the mouth seal-forming structure 3062 is constructed from a biocompatible material, e.g. silicone rubber.

A nasal seal forming structure 3052 and/or the mouth seal-forming structure 3062 in accordance with the present technology may be constructed from a soft, flexible, resilient material such as silicone.

In certain forms of the present technology, a system is provided comprising more than one nasal seal forming structure 3052 and/or the mouth seal-forming structure 3062, each being configured to correspond to a different size and/or shape range. For example the system may comprise one form of a seal-forming structure suitable for a large sized head, but not a small sized head and another suitable for a small sized head, but not a large sized head.

5.3.1.1 Sealing Mechanisms

In one form, the nasal seal-forming structure 3052 and/or the mouth seal-forming structure 3062 includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the nasal seal-forming structure 3052 and/or the mouth seal-forming structure 3062 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the nasal seal-forming structure 3052 and/or the mouth seal-forming structure 3062 may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the nasal seal-forming structure 3052 and/or the mouth seal-forming structure 3062 comprises a tension portion. In use, the tension portion is held in tension, e.g. by adjacent regions of the sealing flange.

In one form, the nasal seal-forming structure 3052 and/or the mouth seal-forming structure 3062 comprises a region having a tacky or adhesive surface.

In certain forms of the present technology, the nasal seal-forming structure 3052 and/or the mouth seal-forming structure 3062 may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.7 Nasal and/or Mouth Cushion

FIGS. 4A to 6D show the seal-forming structure 3052 of the nasal cushion 3050 according to an example of the present technology. In the illustrated example, the seal-forming structure 3052 may be considered a nasal cradle cushion and intended to provide a flow of pressurised gas to the patient's nares by sealing against at least the underside of the patient's nose. The exemplary seal-forming structures 3052 will engage the patient's face below the bridge of the nose and some examples, depending on the size and shape of the patient's nose, may engage the patient's nose below the pronasale. An exemplary seal-forming structures 3052 may also engage the patient's face at least above the upper vermillion. Thus, an exemplary seal-forming structures 3052 may seal against the patient's lip superior in use. Furthermore, the patient's mouth may remain uncovered by the seal-forming structure 3052 of the depicted examples such that the patient may breathe freely, i.e., directly to atmosphere, without interference from the seal-forming structure 3052. In some examples, the nasal seal-forming structure 3052 comprises a nasal cradle cushion, a nasal cushion or pillows adapted to from a seal relative to the entrance of a patient's nose.

FIGS. 4A to 6D show the seal-forming structures 3052 and 3062 of the nasal cushion 3050 and the mouth cushion 3060, respectively, according to an example of the present technology. In some examples, the combined nasal cushion 3050 and mouth cushion 3060 may be referred to as a full face cushion or oro-nasal cushion. In the illustrated example, the seal-forming structure 3062 may provide a flow of pressurized gas to the patient's mouth by sealing against at least a portion around the patient's mouth. The exemplary seal-forming structures 3062 will engage the patient's face around the mouth. In some example, the seal-forming structures may also engage underside of the patient's nose and/or the patient's face below the bridge of the nose. An exemplary seal-forming structures 3062 may engage the patient's face above the upper lip vermillion and/or below the lower lip vermillion. Thus, an exemplary seal-forming structures 3062 may seal a portion of the patient's face around the mouth in use. In some forms of the present technology, the mouth cushion 3060 may include a second nasal cushion, or the mouth cushion may not include the nasal cushion. In some forms of the present technology, the mouth cushion 3062 and the nasal cushion 3050 are releasably connected to one another.

The exemplary nasal cradle cushion may include a superior saddle or concave region that has positive curvature across the cushion. Also, the nasal cradle cushion may be understood to have a single target seal forming region or surface, in contrast to a pillows cushion may have two target seal forming regions (one for each naris). Cradle cushions may also have a posterior wall that contacts the patient's lip superior and an upper, central, surface contacts the underside of the patient's nose. These two surfaces on the patient's face may form a nasolabial angle between them (see FIG. 2E). A cradle cushion may be shaped to have a nasolabial angle within the range of 90 degrees to 120 degrees.

Furthermore, the exemplary seal-forming structure 3052 may also be shaped and dimensioned such that no portion of the seal-forming structure 3052 enters into the patient's nares during use.

In an example, the exemplary seal-forming structure 3052 and/or 3062 may include at least two regions of different thickness. In an example, the differing thicknesses may be produced by extending regions of different thickness different distances into the interior of the seal-forming structure 3052 and/or 3062 such that the exterior surface of the seal-forming structure 3052 and/or 3062 remains smooth. The exterior surface may not be uneven at transitional areas between the regions of different thickness. Thus, the exterior of the exemplary seal-forming structures 3052 and/or 3062 is continuous and smooth.

In an example, naris openings may be formed to generally align with patient's corresponding naris to provide the flow of pressurised gas to the patient's nares for inhalation.

In an example, the seal-forming structure 3052 and/or 3062 in different examples may be sized and shaped differently and, accordingly, each variation may provide an optimal fit for patients having noses and faces shaped and sized differently.

In an example, the seal-forming structure 3052 and/or 3062 may include two or more different sizes/shapes. For example, size dimensions and/or contours of the seal-forming structure may be varied to provide alternative seal forming surfaces for different patients.

In an example, one or more thickened portions (e.g., thickened portion of silicone) may be provided to one or more regions of the seal-forming structure 3052 and/or 3062 to add support and stability to the one or more regions, e.g., to ensure cushion stability and seal performance. In an example, the one or more thickened portions may be produced by increasing the thickness of the seal-forming structure 3052 and/or 3062 in one or more regions into the interior of the seal-forming structure 3052 and/or 3062 such that the exterior surface of the seal-forming structure 3052 and/or 3062 remains continuous and smooth. The one or more thickened portions may include similar or different thicknesses relative to one another. In an example, the thickness of thickened portion(s) and/or the specific positioning of the thickened portion(s) along the seal-forming structure 3052 and/or 3062 may be at least partially dependent on the size of the seal-forming structure 3052 and/or 3062.

5.3.2 Frame

In an example, the nasal seal-forming structure 3052 and/or the mouth seal-forming structure 3062 may be connected to a frame.

The frame may be permanently (e.g., overmolded) or removably (e.g., interference fit assembly) connected to the seal-forming structure. For example, the nasal seal-forming structure 3052 and/or the mouth seal-forming structure 3062 may be connected to a frame which together comprise an overmolded construction to form a one-piece integrated component.

5.3.3 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3052 and/or 3062. The seal-forming structure 3052 and/or 3062 may extend in use about the entire perimeter of the plenum chamber 3200. In some forms, the plenum chamber 3200 and the seal-forming structure 3052 and/or 3062 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.4 Positioning and Stabilising Structure

The nasal seal-forming structure 3052 and/or the mouth seal-forming structure 3062 of the patient interface 3000 of the present technology may be held in sealing position in use by the positioning and stabilising structure 3300. The positioning and stabilising structure 3300 may ensure that the seal-forming structure installed on the patient interface 3000 is properly positioned and stabilized. Because the shapes and sizes of the seal-forming structures may be different due to the type of cushion (e.g., nasal cushion and/or mouth cushion) attached to the patient interface 3000, the position and/or surface area of a person's face pressed against the cushion may be different for each cushion type. To improve the seal and conform of the person using the patient interface, examples of the present technology provide a positioning and stabilising structure 3300 that is configurable and adjustable to provide a therapeutically effective position and seal for different cushion types.

FIGS. 4A and 9 show a patient interface 3000 providing a configurable or modular positioning and stabilising structure 3300 for different cushion types. A first type of headgear 3800 and clips 3810 may be used when a nasal cushion 3050 is attached to the headgear sections 3010 and 3020, and a second type of headgear 3900 and clips 3910 may be used when a mouth cushion 3060 is attached to the headgear sections 3010 and 3020.

The positioning and stabilizing structure 3300 is configured to provide a force to hold (1) the nasal seal-forming structure 3052 or (2) the nasal seal-forming structure 3052 and the mouth seal-forming structure 3062 in a therapeutically effective position on a patient's head. The positioning and stabilizing structure 3300 can be configured in a nasal headgear configuration when the nasal cushion 3050 with the nasal seal-forming structure 3052 is coupled to the headgear sections 3010 and 3020, and can be configured in an oro-nasal headgear configuration when the mouth cushion 3060 with the mouth seal-forming structure 3062 is coupled to the headgear sections 3010 and 3020 (e.g., via a one or more straps). In some examples, the oro-nasal headgear configuration may be used when both the nasal cushion 3050 and the mouth cushion 3060 are attached to the headgear sections 3010 and 3020. In some examples, the mouth cushion 3060 includes an under the chin support, or does not include a chin support.

In the nasal headgear configuration, a pair of nasal headgear clips 3810 connect a nasal headgear 3800 to the first and second headgear sections 3010 and 3020 at a first angle and/or position to ensure appropriate nasal headgear forces are applied to the nasal seal-forming structure 3052.

In the oro-nasal headgear configuration, a pair of oro-nasal headgear clips 3910 connect the oro-nasal headgear 3900 to the first and second headgear sections 3010 and 3020 at a second angle and/or position to ensure appropriate oro-nasal forces are applied to the oro-nasal seal forming structure. The first angle and/or position may be different from the second angle and/or position. In one example, the first and second angles may indicate the direction a main headgear strap extends from the clip slots relative to the headgear sections 3010, 3020, common connecting elements 3980, or Frankfort horizontal.

As shown in FIGS. 4A, 4B, and 4C, while the nasal headgear clips 3810 and the oro-nasal headgear clips 3910 have different shapes providing different headgear positioning, they have connectors that are configured to connect to a pair of common connecting elements 3980 (e.g., common backstrap interface), one connecting element disposed on the first headgear section 3010 and the other connecting element disposed on the second headgear sections 3020. In an example, the clips may be constructed (e.g., molded) of a relative rigid material, e.g., polypropylene, polycarbonate. In another example, the clips may be constructed of a fabric material (e.g., a laminate of a fabric patient-contacting layer, a foam inner layer and a fabric outer layer).

The nasal headgear 3800 and the oro-nasal headgear 3900 may include different strap configurations to provide a therapeutically effective position and seal. With reference to FIGS. 4A, 4B, and 4C, the nasal headgear 3800 may include a single strap connected between the nasal headgear clips 3810. The oro-nasal headgear 3900 may include a first strap 3920 connected between the oro-nasal headgear clips 3910, a second strap 3930 including ends that are removably coupled to the mouth cushion 3060 via headgear cushion interface 3950, and a third strap 3940 connecting the first strap to the second strap 3930. Length of one or more of the straps in the nasal headgear 3800 and/or the oro-nasal headgear 3900 may be adjustable to provide a therapeutically effective position and seal.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises one or more straps constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises one or more straps that are extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first the being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises one or more straps constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another suitable for a small sized head, but not a large sized head.

In certain forms of the present technology, a system is provided comprising more than one positioning and stabilizing structure 3300, each being configured to provide a retaining force to correspond to whether a nasal cushion 3050 or nasal cushion 3050 with a mouth cushion 3060 is used. The first and/or second headgear sections may include common modular conduit that can used for both configurations, and interchangeable sections of the headgear (e.g., straps and cushions).

5.3.4.1 Nasal Headgear Configuration

FIGS. 5A-5D show a patient interface 3000 including a positioning and stabilising structure 3300 that is configured in the nasal headgear configuration when a nasal cushion 3050 is used, according to an example of the present technology. In the illustrated example, the positioning and stabilising structure 3300 is configured to provide a force to hold the nasal seal-forming structure 3052 in a therapeutically effective position on a patient's head in use. As illustrated, each of the first and second headgear sections 3010, 3020 is adapted to extend towards the nasal cushion 3050 from a rear of the patient's head, e.g. a superior portion of the posterior of the patient's head, e.g., at or along the crown or parietal bones.

The first and second headgear sections 3010, 3020 together with the nasal cushion 3050 form a loop. Each of the first and second headgear sections 3010, 3020 is adapted to pass along a patient's cheek, under a patient's eye, and between the patient's eye and ear towards a superior position at the rear of the patient's head.

The first headgear section 3010 and/or the second headgear section 3020 may comprise a hollow tube configured to convey pressurized gas at the therapeutic pressure from another portion of the headgear (e.g., near the rear or crown of the patient's head) to the nasal cushion 3050 for breathing by the patient. In one example, the first headgear section 3010 and/or the second headgear section 3020 are configured to convey pressurized gas at the therapeutic pressure from the rear or crown of the patient's head to the nasal and/or mouth cushion for breathing by the patient. The ends of the hollow tube may be configured to support the nasal and/or mouth cushion in position on the patient's face.

In one form of the present disclosure, first headgear section 3010 and/or the second headgear section 3020 may comprise a fabric strap.

In an example, the first headgear section 3010 may include a left common cushion interface 3012 and the second headgear section 3020 may include a right common cushion interface 3022 for removably or releasably coupling to the nasal cushion 3050 and/or the mouth cushion 3060. The left common cushion interface 3012 and/or the right common cushion interface 3022 may receiving smaller protruding coupling sections of the nasal cushion 3050 and secure the nasal cushion 3050 between the first and second headgear sections.

In an example, at least one feature is provided to maintain patency of the hollow tube. For example, the at least one feature may include a rib or a ring that resists closure of the hollow tube.

In some examples, one or both of the first headgear section 3010 and the second headgear section 3020 may include a strap (e.g., adjustable strap), instead of providing a hollow tube. In this example, the pressurized air may be provide via the headgear section including a hollow tube or directly to the nasal cushion 3050.

In an example, the first headgear section 3010 and/or the second headgear section 3020 may comprise a textile material and/or elastomeric material (e.g., silicone).

In an example, the positioning and stabilizing structure may comprise first and second rigidizers, associated with the first headgear section 3010 and/or the second headgear section 3020.

As shown in FIGS. 5A-5D, each of the first headgear section 3010 and the second headgear section 3020 include a pair of common connecting elements 3980. The common connecting elements 3980 may include rigid elongated sections extending along a portion of and permanently connected to the headgear sections. The elongated sections may include a generally u-shaped portion configured to receive a corresponding rounded portion of the nasal headgear clips 3810 or vice-versa.

The nasal headgear 3800 includes a strap 3820 coupled between a pair of nasal headgear clips 3810. The strap 3820 may be adapted to engage a rear of the patient's head. In the illustrated example, the strap 3820 bifurcates into two back strap portions.

Each of the nasal headgear clips 3810 may including slots 3812 to threadably receive ends of the strap 3820 in a length adjustable manner (e.g., hook and loop fastener).

In some examples, the nasal headgear 3800 includes a first strap 3802 and a second strap 3804 that are connected to the nasal headgear clips. The first and second straps may be removably or permanently connected to the nasal headgear clips 3810. The nasal headgear 3800 may include a center part having a split, forming upper and lower strap portions with a space in between and adapted to cup the occupit of the patient's head.

The nasal headgear clips 3810 are configured connect the nasal headgear 3800 to the left and right headgear sections at a first angle and/or position to ensure appropriate nasal headgear forces are applied to the nasal seal-forming structure when the nasal cushion alone is worn by the patient. The nasal headgear clips 3810 may be removably or permanently connected to the strap 3820. The nasal headgear clips 3810 may be configured to exclusively receive nasal headgear straps of the nasal headgear 3800.

5.3.4.2 Oro-Nasal Headgear Configuration

FIGS. 6A-6D show a patient interface 3000 including a positioning and stabilising structure 3300 that is configured in the oro-nasal headgear configuration when a nasal cushion 3050 and a mouth cushion 3060 are used, according to an example of the present technology. The positioning and stabilising structure 3300 is configured to provide a force to hold the nasal seal-forming structure 3052 and the mouth seal-forming structure 3062 in a therapeutically effective position on a patient's head in use. As illustrated, each of the first and second headgear sections 3010, 3020 is adapted to extend towards the nasal cushion 3050 from a rear of the patient's head, e.g. a superior portion of the posterior of the patient's head, e.g., at or along the crown or parietal bones.

The first and second headgear sections 3010, 3020 together with the nasal cushion 3050 and the mouth cushion 3060 form a loop. Each of the first and second headgear sections 3010, 3020 is adapted to pass along a patient's cheek, under a patient's eye, and between the patient's eye and ear towards a superior position at the rear of the patient's head.

The same first and second headgear sections 3010, 3020 and connecting elements 3980 in the nasal headgear configuration can be used in the oro-nasal headgear configuration. Accordingly, the features of the first headgear section 3010 and/or the second headgear section 3020 and connecting elements 3980, discussed above with reference to the nasal headgear configuration, can be applicable to the oro-nasal headgear configuration.

The oro-nasal headgear 3900 includes a strap system coupled between a pair of oro-nasal headgear clips 3910. The strap system of the oro-nasal headgear 3900 may also be removably coupled to the mouth cushion 3060. The strap system may be adapted to engage a rear of the patient's head, and provide a sufficient retention force to the oro-nasal seal forming structure formed by the nasal cushion 3050 and the mouth cushion 3060.

In the illustrated example, the strap system of the oro-nasal headgear 3900 includes a bottom strap section 3955 with each end including connectors 3956 adapted to couple to the mouth cushion 3060, a first upper strap 3957 coupling the first strap to one of the oro-nasal headgear clips 3910 and a second upper strap 3959 coupling the second upper strap 3959 to the other one of the oro-nasal headgear clips 3910. The upper straps 3957 and/or 3959 may be removably or permanently connected to the oro-nasal headgear clips 3910. Length of one or more of the straps may be adjustable. In one example, the bottom strap section 3955 may include buckles 3360 near ends of the strap through which the ends of the strap are threaded to permit the length adjustment.

In some examples, the oro-nasal headgear 3900 includes the nasal headgear 3800 and a bottom strap section 3955 that is releasably connected to the nasal headgear 3800.

The bottom strap section 3955 may be adapted to pass under the patient's ears and/or include a pair of ends 3956 attachable to the mouth cushion 3060. Each of the ends of the bottom strap section 3955 may be removably attached to a cushion clip or magnetic cushion clip that attaches to the mouth cushion 3060. In one example, the ends of bottom strap section 3955 may be threaded through a buckle 3360 to permit the length adjustment.

In one example, the upper straps 3957 and 3959 are connected to the bottom strap section 3955 at an angle that forms the general shape of a "V".

The configuration of the straps and number of straps is not so limited and may include other configurations (see e.g., FIGS. 4A, 4B, and 4C).

The oro-nasal headgear clips 3910 are configured connect the oro-nasal headgear 3900 to the left and right headgear sections at a second angle and/or position to ensure appropriate oro-nasal forces are applied to the oro-nasal seal forming structure when the nasal cushion 3050 and the mouth cushion 3060 are worn by the patient. The oro-nasal headgear clips 3910 may be removably or permanently connected to the upper straps 3957 and/or 3959. Each of the oro-nasal headgear clips 3910 may include slots 3912 to receive ends of the upper straps 3957 and/or 3959. The nasal headgear clips 3810 may be configured to exclusively receive the oro-nasal headgear 3900.

In one form of the present technology, the patient interface 3000 is provided without a forehead support. The nasal headgear configuration or the oro-nasal headgear configuration may be sufficient to provide the needed support and sealing without needing to include a forehead support.

5.3.4.3 Nasal Headgear Clips and Oro-Nasal Headgear Clips Connecting to Common Connecting Elements As illustrated in FIGS. 4A-6D, the first headgear section 3010 and the second headgear section 3020 include common connecting elements 3980 that can releasable couple the nasal headgear clips 3810 and releasable couple the oro-nasal headgear clips 3910 to the first and second headgear sections. The different shape and/or coupling locations for the straps in the nasal headgear clips 3810 and the oro-nasal headgear clips 3910 provide the angle and/or position for the straps coupled to the clips to ensure appropriate forces are applied to provide a nasal seal or the oro-nasal seal.

FIGS. 7A-7E show common connecting elements 3980 that can be used to couple the nasal headgear 3800 and the oro-nasal headgear 3900 to sections of the patient interface 3000, according to an example of the present technology. The common connecting elements 3980 protrude from the outer surface of respective first headgear section 3010 and the second headgear section 3020. The common connecting elements 3980 provide an elongated groove or slider 3982 having a shape and size corresponding to an elongated groove or slider 3990 provided on the nasal headgear clips 3810 and/or the oro-nasal headgear clips 3910. The elongated slider may slide into the groove to removably secure the nasal headgear clips 3810 or the oro-nasal headgear clips 3910 to the first and second headgear sections.

In one form of the present technology, the common connecting elements 3980 includes a receiving end 3984 provided on one distal end and a stop 3986 at an opposite distal end. The receiving end 3984 is configured to receive one end of a connector of the nasal headgear clips 3810 or the oro-nasal headgear clips 3910. The stop 3986 may comprise a tap that at least partially extends outwardly from the inner surface of the groove or outer surface of the slider to prevent the connector (corresponding groove or slider) of the nasal headgear clips 3810 or the oro-nasal headgear clips 3910 from sliding out of the groove or past an end of the slider. In one form, the stop 3986 may extend from inside the groove and to the outer surface of the common connecting element 3980. The stop 3986 may also provide an indication of when the nasal headgear clips 3810 or the oro-nasal headgear clip 3910 has been inserted far enough into the groove 3982. In one form, the stop 3986 may be provided in the groove and/or on the slider to ensure proper depth and/or direction of connection. In one form, the common connecting elements 3980 are provided with a groove and the clips are provided with a slider configured to removably engage the groove.

In one form of the present technology, both ends of the common connecting element 3980 may have receiving ends and the connector of the clips may be inserted into either end of the common connecting elements 3980. In this example, the clips may include a stop to prevent the clips from sling out of the groove 3982.

In one form of the present technology, the groove 3982 may include an irregular shape corresponding to an irregular shape of the connector provided on the nasal headgear clips 3810 and the oro-nasal headgear clips 3910, so that the clips can be inserted with only one orientation. In this example, the person will be able to inserts the clips in a single orientation to ensure that the nasal headgear 3800 and the oro-nasal headgear 3900 are properly positioned and oriented.

The shape and size of the common connecting element 3980 is not limited to the shown and discussed examples, but may include other shapes and sizes (e.g., different grooves) to removably couple the connectors of the nasal headgear clips 3810 and the oro-nasal headgear clips 3910 to the first headgear section 3010 and the second headgear section 3020.

FIG. 8 shows a nasal headgear clips 3810 according to an example of the present technology. FIG. 9 shows an oro-nasal headgear clips 3910 according to an example of the present technology. As shown in FIGS. 8 and 9, while the nasal headgear clip 3810 and the oro-nasal headgear clips 3910 have some features which are similar, the nasal headgear clip 3810 has a shape that is different from a shape of the oro-nasal headgear clips 3910. In the nasal headgear configuration, two nasal headgear clips 3810 may be used to couple the nasal headgear 3800 to the first and second headgear sections. In the oro-nasal headgear configuration, two oro-nasal headgear clips 3910 may be used to couple the oro-nasal headgear 3900 to the first and second headgear sections.

Both of the nasal headgear clip 3810 and the oro-nasal headgear clip 3910 may be substantially wedge-shaped.

The nasal headgear clip 3810 includes a main side 3814 following along the left/right headgear section, an opposite side 3816 for connecting to the nasal headgear 3900, an upper side 3818, and a lower side 3819 provided opposite to the upper side 3818. As shown in FIG. 8, the upper side 3818 may be longer than the lower side 3819. As viewed from the main side, the upper side 3818 is wider than the lower side 3819.

The oro-nasal headgear clip 3910 includes a main side 3914 following along the left/right headgear section, an opposite side 3916 for connecting to the oro-nasal headgear 3900, an upper side 3918, and a lower side 3919 opposite to the upper side 3918. As shown in FIG. 9, the upper side 3918 may be longer than the lower side 3919. As viewed from the main side, the upper side 3918 is wider than the lower side 3919.

With reference to FIGS. 8 and 9, similarities and differences between the nasal headgear clip 3810 and the oro-nasal headgear clip 3910 are present. The main sides 3814 and 3914 of the nasal and oro nasal clips are identical (e.g., in size and/or shape). The upper side 3818 of the nasal headgear clip 3810 is longer than the upper side 3918 of the oro-nasal headgear clip 3910. The opposite side 3816 of the nasal headgear clip 3810 is shorter than the opposite side 3916 of the oro-nasal headgear clip 3910. The lower side 3819 of the nasal headgear clip 3810 may be approximately the same length as the lower side 3919 of the oro-nasal headgear clip 3910.

The nasal headgear clip 3810 and the oro-nasal headgear clip 3910 may include hole 3988 for removably securing the clips when they are inserted into the groove 3982 of the common element 3980. A locking pin may be placed through the hole 3988 and the common element 3980 to secure the clips when the in use. In some example, the groove may include a protruding pin to engage and secure the clips via the hole 3988 when in use.

The nasal headgear clip 3810 and/or the oro-nasal headgear clip 3910 may include indicia indicating with which type of headgear and/or cushion the clips should be used. As shown in FIG. 8, the nasal headgear clip 3810 may include an "N" indicating that the nasal headgear clip 3810 should be used with the nasal cushion 3050 and/or the nasal headgear 3800. As shown in FIG. 9, the oro-nasal headgear clip 3910 may include an "F" (full face) indicating that the oro-nasal headgear clip 3910 should be used with the nasal/mouth cushion and/or the oro-nasal headgear 3900. The nasal headgear clip 3810 and/or the oro-nasal headgear clip 3910 may include an indicia such as a symbol or hole 3988 to indicate the top or bottom of the clip and/or which end of the clip should be inserted into the common connecting element 3980.

The nasal headgear clip 3810 may include a slot 3812 configured to exclusively receive nasal headgear straps of the nasal headgear 3800. The slot 3812 may be formed at a lower portion of the nasal headgear clip 3810. The slot 3812 may be substantially straight and/or formed adjacent to and/or parallel to the opposite side 3816.

The oro-nasal headgear clip 3910 may include a slot 3912 configured to exclusively receive oro-nasal headgear straps of the oro-nasal headgear 3900. The slot 3912 may be formed at an upper portion of the oro-nasal headgear clip 3910. The slot 3912 may be substantially straight and/or formed adjacent to and/or parallel to the opposite side 3916.

In one form of the present technology the slots 3812 and 3912 may have a same shape and size. In another form of the present technology, the slot 3912 of the oro-nasal headgear clips 3910 may have a different size and/or width compared to the slot 3812 of the nasal headgear clip 3810.

In one form of the present technology the slots 3812 and 3912 may be provided at different positions and/or angles relative to the common connecting elements 3980 and/or each other. For example, the nasal headgear clip slot 3812 may be formed at a nasal clip slot angle ($\alpha 1$) relative to the common connecting element 3980, and the oro-nasal headgear clip slot 3912 may be formed at an oro-nasal headgear clip slot angle ($\alpha 2$) that is different than the nasal clip slot angle relative to the common connecting element 3980. In some examples, the nasal clip slot angle ($\alpha 1$) may be larger than the oro-nasal clip slot angle ($\alpha 2$) (see FIGS. 5B and 6B).

In one form of the present technology, each said nasal headgear slot 3812 is positioned at a slot angle and/or position relative to the left/right headgear section that is different than the slot angle and/or position of the oro-nasal headgear slots 3912 relative to the left/right headgear sections. In one example, the slot angle of the nasal headgear slot 3812 and the oro-nasal headgear slot 3912 may be the same but the position relative to the main sides 3814 and 3914 may be different. For example, the nasal headgear slot 3812 may be positioned closer to the main side 3814 and/or lower side 3819 than the oro-nasal headgear slot 3912 is positioned to the main side 3914 and/or lower side 3919, and/or the headgear slot 3812 may be positioned lower relative to the main side 3814 and/or opposite side 3916 than the oro-nasal headgear slot 3912 relative to the main side 3914 and/or opposite side 3916.

In one form of the present technology, each of the pair of nasal headgear clips 3810 and the pair of oro-nasal headgear clips 3910 includes a slot to receive an upper nasal straps strap 3820 of the nasal headgear 3800 or the upper straps 3957, 3959 of the oro-nasal headgear 3900. The oro-nasal headgear clips 3910 are configured to hold upper ends of the upper straps 3957, 3959 at an oro-nasal strap position, and the nasal headgear clips 3810 are configured to hold upper ends of the upper nasal straps 3820 at a nasal strap position, the oro-nasal strap position being different than the nasal strap position relative to the left/right headgear sections and/or main sides 3814, 3914.

The oro-nasal headgear 3900 may include a pair of upper oro-nasal straps 3957, 3959 connectable to the oro-nasal headgear clips 3910 and the nasal headgear includes a pair of upper nasal straps 3820 connectable to the nasal headgear clips 3810. In use, the upper oro-nasal strap position may be higher than the upper nasal strap position relative to the common connecting element 3980.

The oro-nasal headgear clips 3910 are configured to hold upper ends of the upper oro-nasal straps 3957, 3959 at an oro-nasal strap angle (β2), and the nasal headgear clips 3810 are configured to hold upper ends of the upper nasal straps 3820 at a nasal strap angle (β1) that is different from the oro-nasal strap angle relative to the left/right headgear sections or patient's Frankfort horizontal. In some examples, the oro-nasal strap angle (β2) may be smaller than the nasal strap angle (β1). In some examples, the oro-nasal strap angle (β2) is smaller than the nasal strap angle (β1) relative to the patient's Frankfort horizontal (see FIGS. 5A and 5B). In some examples, the oro-nasal strap angle (β2) is larger than the nasal strap angle (β1) relative to the patient's Frankfort horizontal, depending on various features, including intended dealing locations on patient's nose and/or mouth and/or configuration of the headgear straps. The oro-nasal strap angle and the nasal strap angle may be measured from the lower part of the left/right headgear sections. In some examples, the oro-nasal strap angle and the nasal strap angle may be measured between a line corresponding to the slots in the corresponding clips and the Frankfort horizontal.

5.3.5 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 2 or more holes, about 5 to about 50 holes, about 10 to about 40 holes, about 10 to about 20 holes, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

In certain forms the nasal cushion 3050 and the mouth cushion 3060 may include a common vent 3400 (see e.g., FIG. 4A) that can be positioned on the nasal cushion or the mouth cushion. Opening left in the nasal cushion 3050 can be used as a way to connect the nasal cushion 3050 to the mouth cushion 3060. In one example, the vent 3400 may be inserted in the mouth cushion 3060 and the mouth cushion 3060 may be coupled to the nasal cushion 3050 via opening in the nasal cushion 3050 for the vent 3400.

5.3.6 Decoupling Structure(s)

In one form the patient interface 3000 includes at least one decoupling structure, for example, a swivel or a ball and socket.

5.3.7 Connection Port

Connection port 3600 allows for connection to the air circuit 4170.

5.3.8 Forehead Support

In one form, the patient interface 3000 includes a forehead support 3700. For example, FIG. 3A shows a non-invasive patient interface 3000 in accordance with one aspect of the present technology comprising a seal-forming structure 3100, a plenum chamber 3200, a positioning and stabilising structure 3300, a vent 3400, one form of connection port 3600 for connection to air circuit 4170, and a forehead support 3700.

In the example of FIGS. 4 to 8, the patient interface 3000 is provided without a forehead support.

5.3.9 Anti-Asphyxia Valve

In one form, the patient interface 3000 includes an anti-asphyxia valve.

5.3.10 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block of the RPT device 4000 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.4.1 Oxygen Delivery

In one form of the present technology, supplemental oxygen may be delivered to one or more points in the pneumatic path, such as upstream of the pneumatic block, to the air circuit 4170 and/or to the patient interface 3000.

5.5 Glossary

For the purposes of the present technology disclosure, in certain forms of the present technology, one or more of the following definitions may apply. In other forms of the present technology, alternative definitions may apply.

5.5.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. ‘Flow rate’ is sometimes shortened to simply ‘flow’ or ‘airflow’.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient’s respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient’s face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.5.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.5.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young’s Modulus, or an indentation hardness scale measured on a standardised sample size).

- ‘Soft’ materials may include silicone or thermo-plastic elastomer (TPE), and may, e.g. readily deform under finger pressure.
- ‘Hard’ materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.5.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.5.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.5.4 Anatomy 5.5.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.5.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.5.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.5.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space: (description to be inserted here)

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.5.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.5.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.5.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.5.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.5.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.6 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.7 Reference Signs List

| | |
|---|---|
| patient | 1000 |
| bed partner | 1100 |
| non-invasive patient interface | 3000 |
| patient interface | 3000 |
| headgear section | 3010 |
| left common cushion interface | 3012 |
| second headgear section | 3020 |
| right common cushion interface | 3022 |
| nasal cushion | 3050 |
| nasal seal-forming structure | 3052 |
| mouth cushion | 3060 |
| mouth seal-forming structure | 3062 |
| seal-forming structure | 3100 |
| plenum chamber | 3200 |
| chord | 3210 |
| superior point | 3220 |
| inferior point | 3230 |
| positioning and stabilizing structure | 3300 |
| buckle | 3360 |
| vent | 3400 |
| connection port | 3600 |
| rotatable elbow | 3650 |
| forehead support | 3700 |
| nasal headgear | 3800 |
| first strap | 3802 |
| second strap | 3804 |
| nasal headgear slot | 3812 |
| main side | 3814 |
| opposite side | 3816 |
| upper side | 3818 |
| lower side | 3819 |
| upper nasal straps | 3820 |
| oro—nasal headgear | 3900 |
| oro—nasal headgear clip | 3910 |
| oro—nasal headgear slot | 3912 |
| main side | 3914 |
| opposite side | 3916 |
| upper side | 3918 |
| lower side | 3919 |
| first strap | 3920 |
| second strap | 3930 |
| third strap | 3940 |
| headgear cushion interface | 3950 |
| bottom strap section | 3955 |
| connectors | 3956 |
| first upper strap | 3957 |
| second upper strap | 3959 |
| common connecting element | 3980 |
| groove or slider | 3982 |
| receiving end | 3984 |
| stop | 3986 |
| hole | 3988 |
| groove or slider | 3990 |
| RPT device | 4000 |
| air circuit | 4170 |
| humidifier | 5000 |

The invention claimed is:

1. A patient interface to deliver a flow of air at a positive pressure with respect to ambient air pressure to an entrance to a patient's airways including at least the entrance of a patient's nares while the patient is sleeping, to ameliorate sleep disordered breathing, the patient interface comprising:

a nasal mask including a nasal cushion;

an oro-nasal mask including the nasal cushion and a mouth cushion, wherein the nasal cushion forms at least part of a plenum chamber pressurizable to a therapeutic pressure, wherein the nasal cushion comprises a nasal seal-forming structure configured to form a seal with a region of a patient's face surrounding the entrance to the patient's nares, and wherein the mouth cushion forms at least part of the plenum chamber pressurizable to the therapeutic pressure, wherein the mouth cushion comprises a mouth seal-forming structure configured to form a seal with a region of a patient's face surrounding the entrance to a patient's mouth; and a positioning and stabilizing structure configured to provide a force to hold a selected one of the nasal mask and the oro-nasal mask in a therapeutically effective position on a patient's head, wherein the positioning and stabilizing structure is configured to alternatively operate in a nasal headgear configuration and an oro-nasal headgear configuration depending on the selected one of the nasal mask and the oro-nasal mask coupled to the positioning and stabilizing structure, wherein each of the nasal headgear configuration and the oro-nasal headgear configuration of the positioning and stabilizing structure includes a left headgear section and a right headgear section each configured to pass along a patient's cheek under a patient's eye and between the patient's eye and ear, and to extend to the rear or crown of the patient's head, wherein, when the nasal mask is coupled to the positioning and stabilizing structure and the positioning and stabilizing structure is in the nasal headgear configuration, an end of the left headgear section and an end of the right headgear section are configured to connect to the nasal mask, and wherein, when the oro-nasal mask is coupled to the positioning and stabilizing structure and the positioning and stabilizing structure is in the oro-nasal headgear configuration, the end of the left headgear section and the end of the right headgear section are configured to connect to the oro-nasal mask, wherein the nasal headgear configuration of the positioning and stabilizing structure includes a pair of nasal headgear clips and a nasal headgear, the pair of nasal headgear clips configured to connect the nasal headgear to sides of the left and right headgear sections at a first angle and/or position to ensure appropriate nasal headgear forces are applied to the nasal mask when the nasal mask is worn by the patient, wherein the oro-nasal headgear configuration of the positioning and stabilizing structure includes a pair of oro-nasal headgear clips and an oro-nasal headgear, the pair of oro-nasal headgear clips configured to connect the oro-nasal headgear to the sides of the left and right headgear sections at a second angle and/or position to ensure appropriate oro-nasal forces are applied to the oro-nasal mask when the oro-nasal mask is worn by the patient, and wherein the first angle and/or position provided by the nasal headgear configuration is different than the second angle and/or position provided by the oro-nasal headgear configuration.

2. The patient interface according to claim 1, wherein each of the pair of oro-nasal headgear clips are permanently connected to the oro-nasal headgear and/or each of the pair of nasal headgear clips are permanently connected to the nasal headgear.

3. The patient interface according to claim 1, wherein each of the pair of oro-nasal headgear clips include indicia indicating use with the oro-nasal mask and/or nasal oro-nasal headgear, and each of the pair of nasal headgear clips include indicia indicating use with the nasal mask and/or nasal headgear.

4. The patient interface according to claim 1, wherein each of the pair of nasal headgear clips has a shape that is different than a shape of each of the pair of oro-nasal headgear clips.

5. The patient interface according to claim 1, wherein each of the pair of nasal headgear clips and each of the pair of oro-nasal headgear clips is substantially wedgeshaped, with one main side following along respective ones of the left and right headgear sections, an opposite side for connection to the respective one of the nasal headgear and the oro-nasal headgear, an upper side and a lower side, the upper side being wider than the lower side.

6. The patient interface according to claim 5, wherein the main side of each of the pair of nasal headgear clips and each of the pair of oro-nasal headgear clips are identical, and the upper side of each of the pair of nasal headgear clips is longer than the upper side of each of the pair of oro-nasal headgear clips.

7. The patient interface according to claim 1, wherein each of the pair of oro-nasal headgear clips includes a slot configured to exclusively receive a respective oro-nasal headgear strap of the oro-nasal headgear, and each of the pair of nasal headgear clips includes a slot configured to exclusively receive a respective nasal headgear strap of the nasal headgear.

8. The patient interface according to claim 7, wherein the slot of each of the pair of oro-nasal headgear clips has a different size/width compared to the slot of each of the pair of nasal headgear clips.

9. The patient interface according to claim 1, wherein each of the pair nasal headgear clips includes a slot formed at a lower portion of the respective nasal headgear clip, and each of the pair of oro-nasal headgear clips includes a slot at an upper portion of the respective oro-nasal headgear clip.

10. The patient interface according to claim 1, wherein each of the left and right headgear sections includes a common connection element that is releasably connectable with a respective one of the pair of nasal headgear clips and alternatively a respective one of the pair of oro-nasal headgear clips.

11. The patient interface according to claim 10, wherein the common connection element includes a groove or a slider.

12. The patient interface according to claim 11, wherein each of the groove or the slider includes a stop configured to ensure proper depth and/or direction of connection.

13. The patient interface according to claim 11, wherein the common connection element includes the groove, and each of the pair of nasal headgear clips and each of the pair of oro-nasal headgear clips includes a slider.

14. The patient interface according to claim 10, wherein each of the pair of nasal headgear clips includes a nasal headgear clip slot that is substantially straight, and each of the pair of oro-nasal headgear clips includes an oro-nasal headgear clip slot that is substantially straight, the nasal headgear clip slot being formed at a nasal clip slot angle relative to the common connection element, and the oro-nasal clip slot being formed at an oro-nasal clip slot angle that is different than the nasal clip slot angle relative to the common connection element.

15. The patient interface according to claim 1, wherein each of the pair of nasal headgear clips includes a slot to receive a top strap of the nasal headgear, and each of the pair of oro-nasal headgear clips includes a slot to receive a top strap of the oro-nasal headgear.

16. The patient interface according to claim 10, wherein each of the pair of nasal headgear clips includes a nasal headgear slot, and each of the pair of oro-nasal headgear clips includes an oro-nasal headgear slot, each said nasal headgear slot being positioned at a slot angle and/or position relative to respective left and right headgear sections that is different than a slot angle and/or position of each said oro-nasal headgear slot relative to respective left and right headgear sections.

17. The patient interface according to claim 1, wherein the oro-nasal headgear includes a pair of upper oro-nasal straps connectable to respective ones of the pair of oro-nasal headgear clips, and the nasal headgear includes a pair of upper nasal straps connectable to respective ones of the pair of nasal headgear clips.

18. The patient interface according to claim 17, wherein the pair of oro-nasal headgear clips are configured to hold upper ends of the pair of upper oro-nasal straps at an oro-nasal strap position, and the pair of nasal headgear clips are configured to hold upper ends of the pair of upper nasal straps at a nasal strap position, the oro-nasal strap position being different than the nasal strap position relative to the left and right headgear sections.

19. The patient interface according to claim 18, wherein the oro-nasal strap position is higher than the nasal strap position.

20. The patient interface according to claim 17, wherein the pair of oro-nasal headgear clips are configured to hold upper ends of the pair of upper oro-nasal straps at an oro-nasal strap angle, and the pair of nasal headgear clips are configured to hold upper ends of the pair of upper nasal straps at a nasal strap angle, the oro-nasal strap angle being different than the nasal strap angle relative to the left and right headgear sections.

21. The patient interface according to claim 20, wherein the oro-nasal strap angle is smaller than the nasal strap angle.

22. The patient interface according to claim 20, wherein the oro-nasal strap angle is less than the nasal strap angle relative to the patient's Frankfort horizontal.

23. The patient interface according to claim 20, wherein each of the oro-nasal strap angle and the nasal strap angle is measured from a lower part of the left and right headgear sections.

24. The patient interface according to claim 1, wherein the mouth cushion and the nasal cushion are releasably connected to one another.

25. The patient interface according to claim 1, wherein each of the left and right headgear sections includes a fabric strap.

26. The patient interface according to claim 1, wherein each of the left and right headgear sections includes a hollow tube configured to convey pressurized gas at the therapeutic pressure from the rear or crown of the patient's head to the nasal cushion and/or the mouth cushion for breathing by the patient.

27. The patient interface according to claim 26, wherein each said hollow tube supports the nasal cushion and/or the mouth cushion in position on the patient's face.

28. The patient interface according to claim 1, wherein the patient interface is provided without a forehead support.

29. The patient interface according to claim 1, wherein the nasal headgear includes first and second straps that are connected to respective ones of the pair of nasal headgear clips.

30. The patient interface according to claim 29, wherein the first and second straps are permanently connected to respective ones of the pair of nasal headgear clips.

31. The patient interface according to claim 1, wherein the nasal headgear includes a center part having a split, forming upper and lower strap portions with a space in between and configured to cup the occupit of the patient's head.

32. The patient interface according to claim 1, wherein the oro-nasal headgear includes the nasal headgear and a bottom strap section that is releasably connected to the nasal headgear, the bottom strap section including ends that are connectable to the mouth cushion.

33. The patient interface according to claim 1, wherein the oro-nasal headgear includes a pair of upper straps each having an end connected to a respective one of the pair of oro-nasal headgear clips.

34. The patient interface according to claim 33, wherein each of the pair of upper straps are permanently connected to respective ones of the pair of oro-nasal headgear clips.

35. The patient interface according to claim 1, wherein the oro-nasal headgear includes a bottom strap section configured to pass under the patient's ears, the bottom strap section including a pair of ends attachable to the mouth cushion.

36. The patient interface according to claim 35, wherein the oro-nasal headgear includes a pair of upper straps connected to the bottom strap section at an angle that forms the general shape of a "V".

37. The patient interface according to claim 35, wherein each of the ends of the bottom strap section is attached to a cushion clip or magnetic cushion clip that attaches to the mouth cushion.

38. The patient interface according to claim 1, wherein the nasal headgear and the oro-nasal headgear are length adjustable.

39. The patient interface according to claim 1, wherein each of the left and right headgear sections is releasably connected to the nasal cushion.

40. The patient interface according to claim 1, further comprising a crown piece connecting the left and right headgear sections, the crown piece including an opening that receives a rotatable elbow.

41. The patient interface according to claim 1, wherein the nasal seal-forming structure comprises a nasal cradle cushion, a nasal cushion or pillows configured to form a seal relative to the entrance of a patient's nose.

42. The patient interface according to claim 1, wherein the mouth cushion includes an under the chin support, or does not include a chin support.

43. A CPAP system for providing gas at positive pressure for respiratory therapy to a patient, the CPAP system comprising:

an RPT device configured to supply a flow of gas at a therapeutic pressure;

a patient interface to deliver the gas at the positive pressure with respect to ambient air pressure to an entrance to a patient's airways including at least the entrance of a patient's nares while the patient is sleeping, to ameliorate sleep disordered breathing; and an air delivery conduit configured to pass the flow of gas at the therapeutic pressure from the RPT device to the patient interface, wherein the patient interface comprises:

a nasal mask including a nasal cushion;

an oro-nasal mask including the nasal cushion and a mouth cushion, wherein the nasal cushion forms at least part of a plenum chamber pressurizable to the therapeutic pressure, wherein the nasal cushion comprises a nasal seal-forming structure configured to form a seal with a region of a patient's face surrounding the entrance to the patient's nares, and wherein the mouth cushion forms at least part of the plenum chamber pressurizable to the therapeutic pressure, wherein the mouth cushion comprises a mouth seal-forming structure configured to form a seal with a region of a patient's face surrounding the entrance to a patient's mouth; and a positioning and stabilizing structure configured to provide a force to hold a selected one of the nasal mask and the oro-nasal mask in a therapeutically effective position on a patient's head, wherein the positioning and stabilizing structure is configured to alternatively operate in a nasal headgear configuration and an oro-nasal headgear configuration depending on the selected one of the nasal mask and the oro-nasal mask coupled to the positioning and stabilizing structure, wherein each of the nasal headgear configuration and the oro-nasal headgear configuration of the positioning and stabilizing structure includes a left headgear section and a right headgear section each configured to pass along a patient's cheek under a patient's eye and between the patient's eye and ear, and to extend to the rear or crown of the patient's head, wherein, when the nasal mask is coupled to the positioning and stabilizing structure and the positioning and stabilizing structure is in the nasal headgear configuration, an end of the left headgear section and an end of the right headgear section are configured to connect to the nasal mask, and wherein, when the oro-nasal mask is coupled to the positioning and stabilizing structure and the positioning and stabilizing structure is in the oro-nasal headgear configuration, the end of the left headgear section and the end of the right headgear section are configured to connect to the oro-nasal mask, wherein the nasal headgear configuration of the positioning and stabilizing structure includes a pair of nasal headgear clips and a nasal headgear, the pair of nasal headgear clips configured to connect the nasal headgear to sides of the left and right headgear sections at a first angle and/or position to ensure appropriate nasal headgear forces are applied to the nasal mask when the nasal mask is worn by the patient, wherein the oro-nasal headgear configuration of the positioning and stabilizing structure includes a pair of oro-nasal headgear clips and an oro-nasal headgear, the pair of oro-nasal headgear clips configured to connect the oro-nasal headgear to the sides of the left and right headgear sections at a second angle and/or position to ensure appropriate oro-nasal forces are applied to the oro-nasal mask when the oro-nasal mask is worn by the patient, and wherein the first angle and/or position provided by the nasal headgear configuration is different than the second angle and/or position provided by the oro-nasal headgear configuration.

* * * * *